(12) United States Patent
Vogt et al.

(10) Patent No.: US 10,286,370 B2
(45) Date of Patent: May 14, 2019

(54) STORAGE AND MIXING SYSTEM FOR PASTY CEMENT COMPONENTS AND METHOD THEREFOR

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 217 days.

(21) Appl. No.: 15/451,958

(22) Filed: Mar. 7, 2017

(65) Prior Publication Data
US 2017/0259233 A1      Sep. 14, 2017

(30) Foreign Application Priority Data

Mar. 10, 2016   (DE) .................. 10 2016 104 410

(51) Int. Cl.
*B01F 3/10* (2006.01)
*B01F 15/02* (2006.01)
(Continued)

(52) U.S. Cl.
CPC ...... *B01F 15/0087* (2013.01); *A61B 17/8805* (2013.01); *A61B 17/8825* (2013.01);
(Continued)

(58) Field of Classification Search
CPC ............ A61B 17/8825; A61B 17/8833; A61B 2017/883; A61L 24/06; B01F 13/0023;
(Continued)

(56) References Cited

U.S. PATENT DOCUMENTS

| 2,446,501 A | 8/1948 | Weber |
| 4,493,436 A * | 1/1985 | Brokaw ............ B05C 17/00553 |
| | | 222/137 |

(Continued)

FOREIGN PATENT DOCUMENTS

| DE | 25 21 392 | 11/1976 |
| DE | 201 06 406 U1 | 8/2002 |

(Continued)

OTHER PUBLICATIONS

Australian Office Action for corresponding Australian application No. 2017201617 dated May 23, 2018.

(Continued)

*Primary Examiner* — Tony G Soohoo
(74) *Attorney, Agent, or Firm* — Norris McLaughlin, P.A.

(57) ABSTRACT

A storage and mixing system, for pasty two-component polymethyl methacrylate bone cements, comprises a cartridge with a cylindrical interior, a cartridge head that closes an end of said cartridge, a partition wall axially disposed in the cylindrical interior of the cartridge, wherein said partition wall is connected to the circumferential surface of the cylindrical interior of the cartridge and divides the cylindrical interior of the cartridge delimited by the cartridge head into two spatially separate cavities. The first cavity includes a first pasty cement component and the separate second cavity includes a second pasty cement component, two delivery plungers close the two cavities on the side of the cavities opposite the cartridge head. At least two cutting edges are disposed on the front side of the sleeve-shaped connecting means facing the cartridge head, such that the at least two cutting edges cut off the partition wall from the cylindrical inner wall of the cartridge as at least one cut-off strip when the delivery plungers are advanced towards the cartridge head in the cavities with the connecting means, and wherein the sleeve-shaped connecting means comprises a (Continued)

deflecting surface which is inclined to the axis of the connecting means which, on advancing the connecting means, presses the at least one cut-off strip of the partition wall towards the inner wall of the cartridge.

24 Claims, 12 Drawing Sheets

(51) Int. Cl.
  *B01F 15/00*     (2006.01)
  *A61B 17/88*     (2006.01)
  *B05C 17/01*     (2006.01)
  *B05C 17/005*     (2006.01)
  *B65D 81/32*     (2006.01)
  *B01F 5/06*     (2006.01)
  *A61L 24/06*     (2006.01)

(52) U.S. Cl.
  CPC .......... *A61B 17/8833* (2013.01); *A61L 24/06* (2013.01); *B01F 3/10* (2013.01); *B01F 5/0614* (2013.01); *B01F 15/00506* (2013.01); *B01F 15/0212* (2013.01); *B65D 81/325* (2013.01); *A61B 2017/8838* (2013.01); *A61L 2430/02* (2013.01); *B01F 5/0615* (2013.01); *B01F 15/0226* (2013.01); *B01F 15/0237* (2013.01); *B01F 2215/0029* (2013.01); *B01F 2215/0431* (2013.01); *B05C 17/00509* (2013.01); *B05C 17/00513* (2013.01); *B05C 17/00553* (2013.01); *B05C 17/00576* (2013.01); *B05C 17/00593* (2013.01); *B05C 17/0106* (2013.01)

(58) Field of Classification Search
  CPC ........... B01F 15/00506; B01F 15/0087; B01F 15/0212; B01F 15/0237; B01F 2215/0029; B01F 3/10; B01F 5/0164; B05C 17/00509; B05C 17/00513; B05C 17/00553; B05C 17/00576; B05C 17/00593; B05C 17/0106

See application file for complete search history.

(56) References Cited

U.S. PATENT DOCUMENTS

| | | | |
|---|---|---|---|
| 6,302,574 B1 | 10/2001 | Chan | |
| 6,769,564 B2 | 8/2004 | Prestele | |
| 6,935,541 B1 | 8/2005 | Campbell et al. | |
| 6,938,797 B2 | 9/2005 | Brugner et al. | |
| 7,793,800 B2* | 9/2010 | Griesbaum | B05C 17/00559 222/137 |
| 8,544,683 B2* | 10/2013 | Springhorn | B05C 17/00553 222/1 |
| 8,561,845 B2 | 10/2013 | Reidt et al. | |
| 9,227,218 B1* | 1/2016 | Lin | B65D 83/0033 |
| 9,757,763 B2* | 9/2017 | DiSiro | B05C 17/00516 |
| 10,166,057 B2* | 1/2019 | Vogt | A61B 17/8833 |
| 2001/0004682 A1 | 6/2001 | Keller et al. | |
| 2002/0108971 A1* | 8/2002 | Lafond | B05O 17/0103 222/333 |
| 2002/0153377 A1 | 10/2002 | Prestele | |
| 2004/0074927 A1 | 4/2004 | Lafond | |
| 2004/0129122 A1 | 7/2004 | Brugner et al. | |
| 2009/0105144 A1 | 4/2009 | Vogt et al. | |
| 2009/0105366 A1 | 4/2009 | Vogt et al. | |
| 2009/0266843 A1* | 10/2009 | Griesbaum | B05C 17/00559 222/137 |
| 2016/0023236 A1* | 1/2016 | Lin | B65D 83/0033 222/80 |

FOREIGN PATENT DOCUMENTS

| | | |
|---|---|---|
| DE | 202005010206 U1 | 9/2005 |
| DE | 102007052116 A1 | 4/2009 |
| DE | 102007050762 B3 | 5/2009 |
| DE | 102008030312 A1 | 1/2010 |
| DE | 20 2014 102 416 U1 | 7/2014 |
| DE | 10 2013 107 955 A1 | 1/2015 |
| EP | 0 119 847 A2 | 9/1984 |
| EP | 1 392 450 B1 | 7/2005 |
| JP | S59-187569 A | 10/1984 |
| JP | 2007-502241 A | 2/2007 |

OTHER PUBLICATIONS

English translation Chinese Office Action for corresponding Chinese application 201710141659.2 dated Sep. 5, 2018.

Kuehn, Klaus-Dieter; "Knochenzemente fuer die Endoprothetik"; Springer-Verlag, 2000, pp. 18-19, Springer- Verlag of BertelmannSpringer publishing group, Berlin, Germany.

* cited by examiner

STORAGE AND MIXING SYSTEM FOR PASTY CEMENT COMPONENTS AND METHOD THEREFOR

This application claims foreign priority benefit under 35 U.S.C. 119 of German Application No. DE 10 2016 104 410.5 filed Mar. 10, 2016.

DESCRIPTION OF DISCLOSURE

The invention relates to a storage and mixing system for pasty two-component polymethyl methacrylate bone cements, the storage and mixing system comprising a tubular cartridge with a cylindrical interior.

The invention also relates to a method for mixing pasty cement components into a cement dough, particularly a pasty polymethyl methacrylate bone cement using such a storage and mixing system.

The subject matter of this invention is therefore a simple storage and mixing system for pasty two-component polymethyl methacrylate bone cements that is inexpensive to produce and that allows manual mixing and delivery of the highly viscous pasty components of the polymethyl methacrylate bone cement, even with manually operated delivery devices. The storage and mixing system is to allow mixing and delivery of highly viscous pasty components of two-component polymethyl methacrylate bone cements using manually operated extrusion devices.

Conventional polymethyl methacrylate bone cements (PMMA bone cements) are composed of a powdered component and a liquid monomer component (K.-D. Kühn: Knochenzemente für die Endoprothetik: Ein aktueller Vergleich der physikalischen and chemischen Eigenschaften handelsüblicher PMMA-Zemente. [Bone Cements for End Prosthetics: Up-to-Date Comparison of Physical and Chemical Properties of Commercial PMMA Cements] Springer-Verlag Berlin Heidelberg N.Y., 2001). These polymethyl methacrylate bone cements are applied as cement dough after mixing the cement powder with the liquid monomer component in an uncured, pasty state. When using mixing systems, the cement dough from powdered/liquid cements is located in a cartridge. The cement dough is pressed out of this cartridge by moving a delivery plunger. The delivery plungers typically have a diameter between 30 mm and 40 mm and thus have an area of 7.0 cm$^2$ to 12.5 cm$^2$ at the outer side where the tappet of the delivery device makes contact in the delivery process. The movement of the delivery plunger is caused by manually operated mechanical delivery devices, which are also called applicators. These delivery devices or applicators typically have a press-out force in the range from about 1.5 kN to 3.5 N.

Pasty two-component bone cements as known, for example, from DE 10 2007 050 762 B3, DE 10 2008 030 312 A1 and DE 10 2007 052 116 B4 represent a more recent development. In these two-component bone cements, two pasty cement components are stored in two separate cartridges with two separate delivery plungers. During application, two pastes are pressed out from the cartridges into a static mixer by the movement of the delivery plungers and, after intermixing, are delivered through a delivery pipe. If the pasty cement components have a suitable composition, a non-sticky cement dough ready for application is obtained immediately after the two cement components are intermixed. This eliminates the waiting times for the cement dough to become non-sticky, which inevitably occur when using conventional polymethyl methacrylate bone cements. This saves valuable operating time.

Own experiments as part of the present invention have shown that there is a very great pressure drop at the static mixer in the delivery pipe during the press-out process from the cartridges due to the high viscosity of the pasty cement components. Own experiments have further shown that a press-out force greater than 7 kN is required to extrude the highly viscous cement pastes at an acceptable application rate for medical users when using a conical delivery pipe having a total length of about 17 cm and an inner diameter of 11 mm at the cartridge head and ten static mixing elements.

When applying the previous, conventional PMMA bone cements consisting of a liquid monomer component and a separately stored cement powder component, the cement dough that is formed after intermixing the two cement components in the cementing systems or vacuum cementing systems is pressed out using manually operated delivery devices. These simple mechanical delivery devices predominantly use clamping rods that are driven by a manually operated rocker arm for extruding. The manually operated delivery devices have been tested worldwide for decades and represent the state of the art. It is an advantage of these delivery devices that a medical user can feel the penetration resistance to the bone cement dough when it is pressed into the bone structures (spongiosa) via the manual force he or she must apply.

When using highly viscous pasty cement components in cartridges in which the delivery plungers have an overall area in the range from 7.0 cm$^2$ to 12.5 cm$^2$ at the outer plunger sides that contact the tappets of the delivery devices, these devices can be operated manually with either a very great use of force or not at all. Medical users in the operating theater cannot be expected to apply such great force.

Electrically operated extrusion devices are known from the field of adhesives and sealants. These devices can be operated using accumulators and batteries as well as a stationary power supply unit. Some of these devices can apply very great press-out forces and are capable of extruding particularly tough pasty masses. However, using electric motors has the disadvantage that they contain non-ferrous metals and are costly. Such devices must be painstakingly sterilized or even replaced in the operating theater area that must be kept sterile. Electrical cabling can also hinder a user's movement in the operating theater.

Pneumatic devices have also been proposed. These devices require a stationary or mobile compressed air connection (U.S. Pat. No. 2,446,501 A; DE 20 2005 010 206 U1). They also require compressed air hoses that can hinder a user's movement.

Alternatively, compressed gas cartridges can be used to provide pressurized gas. Devices were proposed for this purpose in which the pressurized gas inflow is controlled by a valve and the viscous mass flow is controlled by a second valve (US 2004/0074927 A1; U.S. Pat. No. 6,935,541 B1). The gas cartridges are integrated in these devices. Such systems that are connected to a compressed air supply or include compressed air cartridges always require a compressed air source, without which these systems can no longer be used.

U.S. Pat. No. 8,544,683 B2 discloses a cartridge system that is suitable for adding a small quantity to a main component. The cartridge system includes a cartridge and a second, smaller cartridge disposed next to it, wherein a delivery plunger in the smaller cartridge is operated via a joint connecting element when a delivery plunger in the larger cartridge is advanced. The connecting element cuts through the cartridge walls to limit the overall length of the system. The disadvantage is that the delivery plungers tend to tilt due to the asymmetrical design of the cartridge system. This effect is particularly pronounced when using highly viscous pasty cement components to produce PMMA bone cement. The cartridge system requires such a great force for extruding and mixing when used with such viscous cement components that conventional manually operated delivery devices cannot provide it.

A coaxial cartridge system containing a special plunger system is described in patent specification EP1 392 450 B1. The cartridge system is used for storing and mixing pasty two-component sealing compounds in chemical plants producing building materials. The plunger system disclosed there has a cylindrical delivery plunger for the central cartridge and an annular delivery plunger, for the second, coaxially disposed cartridge. Both delivery plungers are driven from behind the sealing surfaces by a supporting element that has multiple contact surfaces for the tappet of the delivery device. The supporting element contains arc-shaped cutting edges. Both plungers are advanced towards the cartridge head upon axial action by a tappet of an extrusion device. The pasty components contained in the coaxial cartridges are pressed towards the cartridge head in the process. At the same time, two cutting edges cut the wall of the inner coaxial cartridge into two parts. The disadvantage of this system is that two cutting processes are inevitably carried out simultaneously. This means that energy must be provided for both cutting processes, which will then not be available for the actual advancement of the two pasty components. Mixing pasty cement components for PMMA bone cements needs a lot of driving energy due to the static mixers disposed in the delivery pipe and the high viscosity of the cement components, which cannot be provided manually and safely using larger cartridges and conventional delivery devices. A loss of driving energy due to two simultaneous cutting processes can therefore be problematic, particularly with highly viscous pasty components. In addition, coaxial cartridges cannot easily be filled with cement components of a PMMA bone cement. This is particularly true when only small quantities of PMMA bone cement are to be contained, since the free cross sections of the outer coaxial cartridge become so small that it cannot be filled using conventional methods.

It is therefore the object of the invention to overcome the disadvantages of the prior art. Particularly, a simple storage and mixing system for pasty two-component polymethyl methacrylate bone cements that is inexpensive to produce and a method for producing a cement dough using a storage and mixing system are to be provided, wherein the storage and mixing system should be a one-time, ready to use system of the most simple design, requiring a minimal number of assembly steps that make it ready for use within seconds and which, after being connected to manually operated medical delivery devices or applicators, will produce a homogeneous mixed cement dough immediately after manual operation of the delivery device is begun and deliver it at the outlet opening of the delivery pipe. The manually operated delivery devices used to date for the conventional polymethyl methacrylate bone cements in operating theaters, comprising a push rod and optionally a tray, should be usable for delivering the two-component polymethyl methacrylate bone cement or the cement dough with the storage and mixing system to be developed. This is to avoid the purchase of special delivery devices for delivering pasty two-component polymethyl methacrylate bone cements.

It is preferred that the storage and mixing system to be developed does not require two interconnected push rods or tappets that must be advanced in sync, such that the entire device will not be much longer or larger than the common mixing systems and vacuum mixing systems used to date for the conventional powdered and liquid polymethyl methacrylate bone cements. A simple solution is to be found that allows synchronous and manual delivery of two pasty cement components from the device, using just a push rod or tappet and optionally a tray attached to it. The pasty cement components of the bone cement should be safely and separately storable within the storage and mixing system. The two pasty cement components should be safely combinable for use. The storage and mixing system should also be capable of delivering a low volume of the homogeneously mixed cement dough of about 50 ml up to a maximum of 70 ml, without requiring a great effort to dispose of larger residual amounts (more than 15 ml) remaining in the system. It is not intended for larger volumes of cement dough. The small quantities mentioned will be sufficient for many applications, such as operations in the knee area.

The transition from the cartridge to the delivery pipe should be designed such that the flow resistance of the pasty cement components is as low as possible during pressing out. Pasty cement components must be used as cement components which can be applied immediately after extrusion, that is, which do not need any time for swelling the PMMA bone cement. The device should be designed such that confusion of the relevant assembly steps by the user is largely excluded and the storage and mixing system can be handled by largely untrained personnel. Furthermore, a method is to be provided for mixing the pasty cement components and for delivering the homogeneous mixed cement dough.

The objects of the invention are achieved by a storage and mixing system for pasty two-component polymethyl methacrylate bone cements, the storage and mixing system comprising a) a tubular cartridge with a cylindrical interior, b) a cartridge head that closes one end of the tubular cartridge, c) a partition wall axially disposed in the cylindrical interior of the cartridge, wherein said partition wall is connected to the circumferential surface of the cylindrical interior of the cartridge and wherein the partition wall divides the cylindrical interior of the cartridge delimited by the cartridge head into two spatially separate cavities, wherein the first cavity includes a first pasty cement component and the separate second cavity includes a second pasty cement component, d) two delivery plungers disposed movably in the axial direction in the two cavities of the cartridge, wherein said delivery plungers close the two cavities on the side of the cavities opposite the cartridge head, e) wherein the delivery plungers on the back side opposite the cartridge head are connected to one another via a sleeve-shaped connecting means, wherein at least two cutting edges are disposed on the front side of the sleeve-shaped connecting means facing the cartridge head, such that the at least two cutting edges cut off the partition wall from the cylindrical inner wall of the cartridge as at least one cut-off strip when the delivery plungers are advanced towards the cartridge head in the cavities with the connecting means.

f) wherein the sleeve-shaped connecting means comprises a deflecting surface which is inclined to the axis of the connecting means which, when the connecting means are advanced, presses the at least one cut-off strip of the partition wall towards the inner wall of the cartridge.

The at least two cutting edges can preferably be disposed at the edge of the front side of the sleeve-shaped connecting means facing the cartridge head or the two outermost cutting edges of the at least two cutting edges are disposed at the edge of the front side of the sleeve-shaped connecting means facing the cartridge head. This keeps the width of the remnants of the partition wall remaining on the inner wall of the cartridge as small as possible.

The at least one strip of the partition wall, which is cut off by the at least two cutting edges from the inner wall of the cartridge is therefore separated from the cartridge. It is particularly preferred that the deflecting face deforms the at least one cut-off strip of the partition wall. The deformation causes a shift of the material of the parts of the cut-off part of the partition wall towards the inner wall of the cartridge. It is most particularly preferred that the at least one cut-off strip of the partition wall is pressed against the inner wall of the cartridge.

If the partition wall is very stiff and/or tough, more than two cutting edges can be provided, in order to cut the partition wall into a plurality of strips which can then be more easily deflected or pressed towards the inner wall of the cartridge.

According to the invention, the connecting means preferably has a diameter of at least 1.5 mm, particularly preferred at least 3 mm, at its base opposite the cutting edges. This ensures that a tappet of a delivery device is provided with a sufficient contact area for advancing the connecting means and thus the delivery plunger.

The two cavities are preferably likewise cylindrical and particularly preferably have a base in the shape of a semicircle or in the shape of circle segments.

It is preferred that the storage and mixing system is provided for a 1:1 mixture of the cement components.

It can be provided that the partition wall is at least half as wide as half of the maximum diameter vertically to the axis of the cartridge. It can also be provided that the partition wall is a flat surface. The partition wall is to divide the cylindrical interior of the cartridge in the area of the axis of the interior of the cartridge into two cavities, particularly preferred into two cavities of equal size.

In an alternative further development of the present invention, it is proposed that the delivery plungers consist of multiple parts not connected to one another, preferably a front part and a rear part, which are connectable or placeable next to each other. In that case, the front part is simply advanced into the cavities by the rear part. The connecting means is connected or is connectable to the rear or rearmost parts of the delivery plungers. It is preferred that the two delivery plungers are made in one piece and are firmly attached to the connecting means to stabilize the two delivery plungers and to stabilize the movement of the two delivery plungers in the cavities.

It can preferably be provided that the partition wall divides the interior of the cartridge liquid-impermeably, such that the two cavities are liquid-impermeably separated from one another.

This ensures that the two cement components can be stored for a longer period of time in the storage and mixing system or inside the cartridge, respectively. The liquid and very mobile monomer component should be prevented from seeping into the adjacent cavity and reacting with the other cement component.

According to a preferred further development of the invention, the partition wall is connected to the circumferential surface of the cylindrical interior of the cartridge along two connecting lines that delimit the circumferential surface, wherein these connecting lines are preferably arranged opposite one another and the axis of the cartridge particularly preferably extends in the partition wall.

This allows an even advancement of the delivery plungers in the cavities and an even cutting off of the partition wall at a consistent force.

It can be provided that the side of the connecting means that is facing away from the cartridge head is a contact surface for a tappet of a delivery device. The tappet of the delivery device is preferably oriented in a direction in the surface of the partition wall so that the pressure applied by the tappet onto the cutting edges causes the cutting edges to cut through the partition wall and allows the cut-off strip to be pushed through the connecting means. Blocking of the cut-off strip should be prevented as much as possible.

Furthermore, it can be provided that the cavities have a semicircular or circular segmental cross section and the delivery plungers have a matching cross section, such that the delivery plungers close the cavities at each axial position in the cavities.

This allows the implementation of a particularly simple and low-cost storage and mixing system.

According to a preferred further development of the storage and mixing system according to the invention it can be provided that the delivery plungers are spaced apart by the connecting means such that the gap between the delivery plungers is smaller than or equal to the thickness of the partition wall.

This ensures that the delivery plungers run in a stable way inside the cavities and that the partition wall can be easily cut off by the at least two cutting edges and the at least one cut-off strip can be easily guided through the connecting means.

It can also be provided that the partition wall has a maximum thickness of 1.5 mm, preferably a maximum thickness of 1.0 mm, and/or the partition wall can be of such a thickness that the partition wall is cuttable by the at least two cutting edges, on which acts a driving force of 1 kN.

This ensures that the partition wall, if it is made from the typical plastic materials, can be cut off easily with manually operated delivery devices, while the cement components are pressed out of the cavities by the delivery plungers.

Furthermore, it can be provided that the storage and mixing system includes a delivery pipe that is provided with a fastening means for fastening the delivery pipe to the cartridge, wherein the delivery pipe is preferably fixable to the cartridge instead of the cartridge head.

The fastening means is preferably a female thread that can be screwed onto a male thread on the cartridge. It is particularly preferred that the male thread on the cartridge is also used for detachable fastening of the cartridge head to the cartridge.

According to the invention preferably, a static mixer is disposed in the delivery pipe. The invention also proposes that a static mixer is disposed in the delivery pipe and that a female thread, a male thread, elements of a bayonet joint and/or latching elements of a latch closure are attached as connecting means to the base of the delivery pipe.

The delivery pipe can therefore be used to mix the cement components and to apply them precisely. A longer delivery pipe is advantageous particularly if the locations for applying PMMA bone cement are difficult to access.

All generally known static mixers can be considered for use as static mixers. A female thread and/or a male thread and/or elements of a bayonet joint and/or latching elements of a latching closure are attached to the base of the delivery pipe as connecting means. This connecting means can be used for a stable mechanical connection of the delivery pipe to the cartridge. This connection must be stable so that the high pressure that occurs when the pasty cement components are pressed out does not lead to detachment of the delivery pipe from the cartridge. Particularly advantageous connecting means are threads; double threads are particularly advantageous.

Where the storage and mixing systems have a delivery pipe, it can be provided that the ratio of the diameter of the cartridge interior to the inner diameter of the delivery pipe is smaller than 5 to 2, wherein the ratio of the diameter of the cartridge interior to the inner diameter of the delivery pipe is preferably smaller than or equal to 2 to 1, and, particularly preferably, the ratio of the diameter of the cartridge interior to the inner diameter of the delivery pipe is 8 to 5.

This ensures that there is a sufficient flow rate of the PMMA bone cement at the outlet opening of the delivery pipe while the delivery plunger is advanced.

According to a preferred further development it can also be provided that the diameter of the cartridge interior is smaller than or equal to 25 mm, wherein the diameter of the cartridge interior is preferably smaller than or equal to 20 mm.

In storage and mixing systems with a delivery pipe it can also be provided that the diameter of the cartridge interior is smaller than or equal to 25 mm and the inner diameter of the delivery pipe is smaller than or equal to 15 mm, wherein it is preferred that the diameter of the cartridge interior is smaller than or equal to 20 mm and the inner diameter of the delivery pipe is smaller than or equal to 12 mm.

The design of the cartridge or of the cartridge and the delivery pipe, according to the invention makes it possible for both pasty cement components of the PMMA bone cement to be accommodated in a single cartridge that can still be pressed out by applying manual force and that can also still be filled using conventional techniques. If diameters are greater, manual application of force is no longer easily sufficient to press the viscous pasty cement components of the bone cement out of the cartridge.

According to the invention, it is also proposed that the cartridge is integral with the partition wall disposed therein, preferably, the cartridge and the partition wall are made as a one-piece injection-molded part from plastic.

In this way, the two cavities are separated in a tightly sealed manner, allowing for longer storage of the cement components.

Furthermore, it can be provided that the at least two cutting edges consist of a steel alloy, aluminum alloy, tin alloy, ceramic, polyamide, glass fiber reinforced polyamide, polyimide, polyamide co-imide, polyether ketone or polysulfone.

These materials are suitable for cutting the partition wall and are inexpensive to process.

A further development of the invention proposes that the ratio of the inner cartridge diameter to the distance of the delivery plunger from the cartridge head is smaller than or equal to 1 to 4, wherein the ratio of the inner cartridge diameter to the distance of the delivery plunger from the cartridge head is preferably smaller than or equal to 1 to 10.

According to a further development of the device according to the invention it can be provided that two ducts are provided in the cartridge head that connect the two cavities to the environment of the storage and mixing system, wherein a detachable plug is disposed in these ducts.

In this way, the cement components can be filled in to the cavities through these ducts. In a variant of the present invention, the cement components can be pressed out again through these ducts after the plugs are removed.

In preferred storage and mixing systems, it can also be provided that the cartridge comprises a fastening element for a delivery device on the side opposite the cartridge head and at least one fastening means on the side of the cartridge head, particularly a male thread, a female thread, at least one element of a bayonet joint and/or a latching element of a latching closure as the fastening means.

This makes it easier to connect the cartridge to an extrusion device on the back side or to a delivery pipe and/or a closure of the cartridge head on the front side.

The delivery plungers can be used for filling the cavities with the cement components if they initially rest against the cartridge head. The cement components are pressed into the cavities, and in the process the delivery plungers are pressed towards the fastening means or the back side of the cartridge, and no undesirable air inclusions remain in the interior of the cavities that would interfere with the extrusion of the cement components from the cavities by the delivery plungers. Latching means can be provided that connect the delivery plungers to the connecting means.

Likewise, it can be provided that the cartridge, the cartridge head, the partition wall, and the delivery plungers are made of a plastic material, wherein polyethylene co-vinyl alcohol (EVOH), polybutylene terephthalate (PBT), polyethylene terephthalate (PET) and polymethacrylic acid methyl ester-co-acrylonitrile are preferred plastic materials.

A setup using plastic materials is inexpensive and can easily be implemented. The preferred plastic materials are particularly well-suited due to their resistance to chemicals contained in the cement components.

Furthermore, it can be provided that the cartridge head is implemented by an rubber-elastic plate which is fastened to the cartridge using a sleeve cap, wherein said sleeve cap blocks a movement of the rubber-elastic plate away from the cartridge by means of a projecting rim, and wherein said rubber-elastic plate has a recess for receiving the longitudinal side of the partition wall on the side facing the delivery plungers, and wherein said receptacle in the rubber-elastic plate preferably defines two areas, wherein a duct that is closed by a plug is disposed in each area.

This results in a good sealing effect of the storage and mixing system. The division of the rubber-elastic plate into two areas should not be deemed to mean that the rubber-elastic plate must comprise two separate parts. The two areas can also be contiguous and be formed by an integral rubber-elastic plate.

Furthermore, hereby it can be provided that the cartridge head is provided with an additional plastic plate, wherein said plastic plate is disposed on or under the rubber-elastic plate in the cartridge head. The plastic plate is used for extra sealing and enhances the chemical resistance of the cavities it delimits to the cement components. The arrangement of the extra plastic plate results in an improved diffusion barrier against the methyl methacrylate contained in the cement components.

Furthermore, it can be provided that a sleeve cap is provided as a connecting element for connecting the cartridge head and the cartridge, wherein said sleeve cap includes a female thread or a male thread or a bayonet joint or latching elements.

The sleeve cap is preferably a sleeve nut and can be screwed onto the cartridge. The sleeve cap can be considered a part of the cartridge head. This allows a stable connection of the cartridge head to the cartridge. The connecting element can be used to safely connect the sleeve cap to the cartridge. This safely prevents detachment of the cartridge head from the cartridge during storage and transport.

According to the invention, it can be provided that the cartridge head is formed by an rubber-elastic plate and a sleeve cap made of a plastic material, wherein the sleeve cap blocks the rubber-elastic plate by a projecting rim from moving upwards, wherein the rubber-elastic plate has a recess at its bottom side for receiving the longitudinal side of the partition wall, and wherein said receptacle divides the rubber-elastic plate into two semicircular areas, and wherein a duct is disposed in each semicircular area, said duct being closed by a plug. The two ducts are required for filling the two cavities with the pasty cement components. The sleeve cap can also be considered a part of the cartridge head.

In one configuration variant, the front face of the cartridge is formed as a cartridge head, whereas the bottom side has a recess for receiving the narrow side of the partition wall which divides said front face into two semicircular areas, wherein a duct is disposed in each semicircular area, said duct being closed by a plug. These ducts can be cylindrical, semicircular, circular segmental, or kidney-shaped. The plugs are also cylindrical, semicircular, circular segmental, or kidney-shaped to match the geometry of these ducts. It is particularly advantageous that the plugs have latching elements at their bottom side, which effectively prevents loosening of the plugs from the cartridge head during storage or transportation of the cartridge system.

According to a particularly preferred embodiment of the present invention it can be provided that the sleeve-shaped connecting means on the back side that faces away from the cartridge head comprises a lateral opening, so that the at least one strip of the partition wall cut off from the inner wall of the cartridge exits through said opening laterally out of the connecting means.

As a result, it is achieved that the at least one cut-off strip of the partition wall is guided or routed through the opening and is thus safely steered towards the inner wall of the cartridge, so that said strip does not adversely affect or restrict the movement of the tappet of the delivery device, with which the delivery plungers and the connecting means are driven. In addition, the duct formed by the opening in the connecting means can also be used to reshape the at least one cut-off strip of the partition wall within the connecting means.

Particularly preferred it can be provided that the sleeve-shaped connecting means circumferentially rests against the inner wall of the interior of the cartridge on the side facing the cartridge head. As a result, any lateral opening provided is delimited at the circumferential surface of the sleeve-shaped connecting means towards the front (towards the cartridge head). The cut-off partition wall preferably extends through the interior of the sleeve-shaped connecting means.

As a result of this measure, the sleeve-shaped connecting means can stably slide through the interior of the cartridge, without tilting during the movement of the cartridge in the interior and without the delivery plungers being propelled to varying extents and unevenly forward towards the cartridge head.

In addition, storage and mixing systems according to the invention can be distinguished by the inclined deflecting surface being enclosed in certain regions by the sleeve wall of the sleeve-shaped connecting means, such that the at least one cut-off strip of the partition wall running through the connecting means is curved by the sleeve wall of the connecting means which encloses the inclined deflecting face about the longitudinal axis of the at least one cut-off strip.

The sleeve wall can therefore be used to reshape the at least one partition wall strip, such that the latter can be more easily brought into contact with the inner wall of the cartridge due to its shape, or the risk of an unintentional adverse effect to the drive by means of the tappet of the delivery device is reduced due to the shape.

The objects addressed by the present invention are also achieved by a method for mixing pasty cement components of a pasty cement goal, particularly a polymethyl methacrylate bone cement using such a storage and mixing system, characterized by the following subsequent steps:

a) removing the cartridge head from the cartridge or removing at least two plugs from at least two ducts in the cartridge head, such that the cartridge is opened, b) arranging and connecting a delivery pipe to the opened cartridge, wherein said delivery pipe includes a mixer, c) inserting the cartridge into a manually operated delivery device, said delivery device comprising a tappet that is drivable in the axial direction to advance the delivery plungers in the cavities of the cartridge, and d) extruding the pasty cement components by means of the delivery device through axial advancement of the delivery plungers using the tappet, as a result of which the cement components are pressed into the delivery pipe, wherein the two cement components are mixed into a pasty cement dough by the mixer in the delivery pipe and the mixed cement dough flows out of an outlet opening of the delivery pipe, wherein the partition wall is cut off in the longitudinal direction of the cartridge by the at least two cutting edges in sync with the movement of the delivery plungers, and the at least one cut-off strip of the partition wall is pressed by the deflecting surface towards the inner wall of the cartridge outwards to such an extent that any further movement of the tappet of the delivery device is not prevented or hindered by the at least one strip.

These steps are preferably performed chronological successively. The delivery devices are preferably manually operated.

The cartridge or the cavities of the cartridge in which the cement components are stored are closed before removing the cartridge head from the cartridge or before removing the at least two plugs from the at least two ducts in the cartridge head.

In the case of the method according to the invention it can be provided that the at least one strip of the partition wall is curved by the sleeve wall of the connecting means which encloses the inclined deflecting surface about the longitudinal axis of the at least one cut-off strip.

This ensures that the at least one cut-off strip of the partition wall does not hinder any further movement of the tappet, since the at least one cut-off strip of the partition wall can therefore be more easily brought into contact with the inner wall of the cartridge.

Furthermore, it can be provided that a connecting element that connects the cartridge head and the cartridge is loosened to remove the cartridge head from the cartridge in step a).

This ensures a more stable connection between the cartridge head and the cartridge. In addition, the counterpart on the cartridge, that is, a connecting element on the cartridge, can also be used for connecting the delivery pipe.

According to a preferred further development it can be provided that the delivery pipe is connected to the cartridge by connecting the connecting element of the delivery pipe to a connecting element of the cartridge.

This can ensure that the delivery pipe will not detach from the cartridge when the cement dough is pressed out.

It can also be provided that the tappet of the delivery device applies pressure to the side of the connecting means that faces away from the delivery plungers and the delivery plungers are driven via the connecting means.

The result is that most of the force available from the tappet can be used for driving the cement components and for cutting and deflecting the partition wall. This prevents too great a portion of the force resulting in undesirable deformation of the cartridge or a disturbing tilting of the delivery plungers.

Furthermore, it can be provided that the side of the connecting means that faces away from the delivery plungers comprises a contact surface for making contact with the front side of the tappet or of a tray attached to the same, said contact surface being of equal size or greater than the cross section of the tappet or the support surface of the tray, wherein said contact surface completely covers the cross section of the tappet or the support surface of the tray when the tappet is advanced, or preferably said contact surface exceeds the cross section of the tappet or the support surface of the tray.

Hereby it is achieved that the at least one cut-off strip of the partition wall hinders the movement of the tappet.

It can also be provided that the at least two cutting edges cut off the partition wall directly or close to the inner wall of the cartridge, preferably the partition wall is cut off at a distance of not more than 2 mm from the inner wall of the cartridge off the inner wall of the cartridge, particularly preferably at a distance of not more than 1 mm from the inner wall of the cartridge off the inner wall of the cartridge.

This ensures that no remnants of the partition wall remaining on the inner wall of the cartridge hinder any further movement of the tappet for driving the connecting means.

Finally, the present invention also proposes that the applicator is either manually drivable or is drivable by compressed air or is electrically drivable.

Manually drivable applicators are preferred according to the invention because they neither need to be connected to a compressed air source or a power source nor do they have to contain such a source.

The invention is therefore based on the surprising finding that the cement components can be stored in a single common cartridge with a cylindrical inner space if the cement components are separated from one another in the cartridge by means of a partition wall disposed in the inner space of the cartridge, wherein both delivery plungers can be driven by a common connecting means which cuts out a strip from the partition wall and the at least one cut-off strip of the partition wall is pushed out laterally, such that this will not hinder any further movement of a driving tappet of a delivery device. This makes it possible for manually operated delivery devices with just one tappet to be used, since the required force is sufficient, due to the design according to the invention, to drive and mix the cement components and to cut off and deform the partition wall and/or to push away against the inner wall of the cartridge, or the required force can be completely applied to these four processes. The total force required to advance the cement components, to mix the cement components, and to cut off and bend away the partition wall is not great enough, due to the design according to the invention, that the delivery device would become too difficult to move.

Another surprising finding is that, in this way, a narrow cartridge with just a single delivery plunger can be used to advance the two cement components. This minimizes the force required to mix and extrude the cement components, such that an applicator that can be operated manually can be used together with the storage and mixing system to extrude the cement components from the cartridge and to mix them.

The invention is based on the idea of using just one cylindrical cartridge, rather than multiple side-by-side cartridges or coaxial cartridges, for the separate storage of the two pasty cement components to minimize the flow resistance during delivery. To avoid having to use two push rods and two trays to drive two delivery plungers, the cylindrical cartridge is equipped with an axial and axially cuttable partition wall that divides the inner space of the cartridge defined by two delivery plungers and one cartridge head into two hollow bodies in which the two pasty cement components can be stored separately. Cutting off and bending away a strip of the partition wall can also allow the use of smaller quantities of PMMA bone cement, and even narrower cartridges whose inner spaces have smaller inner diameters can still be pressed out.

In a first embodiment, the cartridge head is removed and the delivery pipe which contains a static mixer is directly connected to the cartridge using a connecting element. Immediately thereafter, the cartridge and the connected delivery pipe are connected to a manually operated delivery device or a manually operated applicator, and delivering the cement components or cement dough is started. These steps require about 3 to 8 seconds to perform. After about 30 seconds of continuous operation of the extrusion device or applicator, delivering the cement dough, that is, the mixed pasty two-component PMMA bone cement, is finished for an overall volume of the two pasty cement components of up to 60 ml, preferably of about 40 ml.

In a second embodiment, two plugs at the cartridge head are removed after removing the partition wall, and the delivery pipe with the static mixer is connected to the cartridge using a connecting element.

The invention is further based on the idea that the first delivery plunger that can be moved in the axial direction is disposed in a first cavity and a second delivery plunger that can be moved in the axial direction is disposed in a second cavity. The partition wall is arranged between the delivery plungers. The delivery plungers are connected on the back sides by a connecting means. The front side of the connecting means is designed as at least two cutting edges oriented vertically to the partition wall. A contact surface for the tappet of a delivery device is configured on the back side of the connecting means. When the connecting means is moved forward towards the cartridge head due to the action of the tappet, the at least two cutting edges behind the delivery plungers make two longitudinal cuts in the partition wall, and the at least one cut-off strip of the partition wall detaches itself from the inner wall of the hollow cylinder. The at least one cut-off strip of the partition wall is pressed outwardly towards the inner wall of the cartridge by a deflecting surface which is inclined at an angle of about 45° to the axis of the cartridge or the direction of movement of the closure means. At the same time, the separated strip of the partition wall is curved at the inner side of the sleeve-shaped connecting means, such that the curvature is parallel to the curvature of the inner side of the cartridge. The cut-out strip of the partition wall then exits as a curved strip through a lateral opening on the back side of the connecting means parallel to the inner side of the cartridge. The tappet of the delivery device can in this way make contact with the contact surface of the connecting means and press the delivery plungers out over the entire length of the hollow body to extrude the pasty cement components.

The invention is further based on the observation that highly viscous cement dough can be delivered from cylindrical cartridges through a delivery pipe with a static mixer in an acceptable amount of time and with acceptable use of manually applied force using commercially available, manually operated extruding devices or applicators, if the delivery plunger has a maximum diameter of 25 mm at its front side. The design according to the invention provides a cartridge system that can utilize such small diameters for highly viscous cement components. Still, the cartridge or the cavities can be filled with cement components without too much of an effort.

An exemplary storage and mixing system according to the invention for pasty two-component polymethyl methacrylate bone cement is composed of a) a tubular hollow body as the cartridge, b) a cartridge head that closes one end of the tubular hollow body, c) a partition wall disposed axially in the tubular hollow body, wherein said partition wall divides the inner space of the hollow body into a first cavity and a second cavity, d) a semicircular first delivery plunger disposed in the first cavity and movable in the axial direction, e) a semicircular second delivery plunger disposed in the second cavity and movable in the axial direction, f) a sleeve-shaped connecting means that connects the back side of the first delivery plunger with the back side of the second delivery plunger, wherein said connecting means spaces the delivery plungers apart, such that the gap between the delivery plungers is smaller than or equal to the thickness of the partition wall, wherein at least two cutting edges are disposed on the front outer sides of the connecting means, wherein a contact surface for the tappet of the delivery device is configured on the back side of the connecting means, g) wherein the thickness of the partition wall is smaller than or equal to 1.5 mm, and h) wherein the cutting edges cut off the partition wall from the inner side of the hollow body behind the first delivery plunger and the second delivery plunger during the forward movement of the connecting means towards the cartridge head, wherein the cut-out partition wall is steered to the side as a strip behind the cutting edges by a deflecting wall of the connecting means located diagonally to the longitudinal axis of the hollow body, wherein the strip-shaped cut-off partition wall is curved by the inner side of the sleeve-shaped connecting means and exits as a curved strip through a lateral opening on the back side of the connecting means, such that the tappet of the delivery device is not hindered in its forward movement towards the cartridge head.

It is an advantage if the hollow cylinder is integral with the partition wall. This eliminates complex assembly steps for inserting a separate partition wall into the hollow cylinder. The use of suitable plastic materials ensures liquid impermeable separation of the two cavities. However, it is also generally possible to insert a separately produced partition wall in the hollow cylinder. The inserted partition wall can be connected to the hollow cylinder by mechanical clamping or welding or gluing.

The highly viscous cement components of pasty polymethyl methacrylate bone cements contain methyl methacrylate, a very volatile, free radical polymerizable monomer. It is therefore indispensable for storing the cement components that the inner walls of the cartridge, the cartridge head, the delivery plungers, and the partition wall are made of plastic materials that provide good diffusion barriers against methyl methacrylate. Preferred plastic materials are polyethylene co-vinyl alcohol (EVOH), polybutylene terephthalate (PBT), polyethylene terephthalate (PET), and polymethacrylic acid methyl ester co-acrylonitrile. In addition, diffusion-tight metal layers, metal or semi-metal oxide layers, or plastic layers can be deposited onto the parts that are not in contact with the cement components. Aluminum layers are particularly suitable as metal layers. Silicon dioxide layers are particularly suitable as semi-metal oxide layers.

The delivery plungers or alternatively the connecting means advantageously have latching elements that can lock in place with mating latching elements on the inner side of the hollow cylinder of the cartridge. These latching elements prevent movement of the delivery plungers in the opposite direction from the cartridge head. Preventing this backward movement is necessary if the cartridge system filled with the cement components is sterilized with ethylene oxide on the outside. When sterilizing with ethylene oxide, a vacuum is applied to the sterilization chamber to remove the air. The resulting negative pressure can cause excess pressure in the cavities due to evaporation of methyl methacrylate in the cement components and thus an undesirable movement of the delivery plunger in the opposite direction from the cartridge head.

It is particularly important that the inner diameter of the cartridge is smaller than or equal to 25 mm so that the required extruding pressure for pressing out and mixing the cement components does not become too high.

An exemplary method according to the invention for mixing the pasty cement components of the pasty polymethyl methacrylate bone cement using the cartridge system can be performed, for example, as follows:

a) removing the cartridge head from the cartridge or removing plugs from the ducts in the cartridge head, b) connecting a delivery pipe that contains a static mixer to the opened cartridge, c) connecting the cartridge to a manually operated extrusion device or delivery device, respectively, d) manual operation of the extrusion device or delivery device, respectively, wherein the tappet presses onto a contact surface of the connecting means, wherein the pasty first cement component is pressed from the first cavity through the first delivery plunger and the pasty second cement component is pressed from the second cavity through the second delivery plunger into the delivery pipe and the static mixer, wherein the mixed cement dough exits at the opening of the delivery pipe, and e) wherein the cutting edges cut the partition wall behind the delivery plungers in the longitudinal direction on both sides of the inner wall of the cartridge synchronously with the forward movement of the delivery plungers, wherein the cut-out strip of the partition wall is steered to the side by a deflecting wall located diagonally to the longitudinal axis of the cartridge, wherein the cut-off strip of the partition wall is curved by the inner side of the sleeve-shaped connecting means and exits as a curved strip through a lateral opening on the back side of the connecting means, such that the tappet of the delivery device is not hindered in its forward movement towards the cartridge head.

In one variant of this method, an extrusion device operated by compressed air or electricity is used in steps d) and e) instead of the manually operated extrusion device.

BRIEF DESCRIPTION OF THE DRAWINGS

Other embodiment examples of the invention will be explained below with reference to twelve schematic figures, without limiting the invention in any way however. Wherein.

DETAILED DESCRIPTION OF THE DISCLOSURE

For the sake of simplicity, the same reference symbols are used in part in the figures for the same and similar components of different embodiments.

Figure 1:
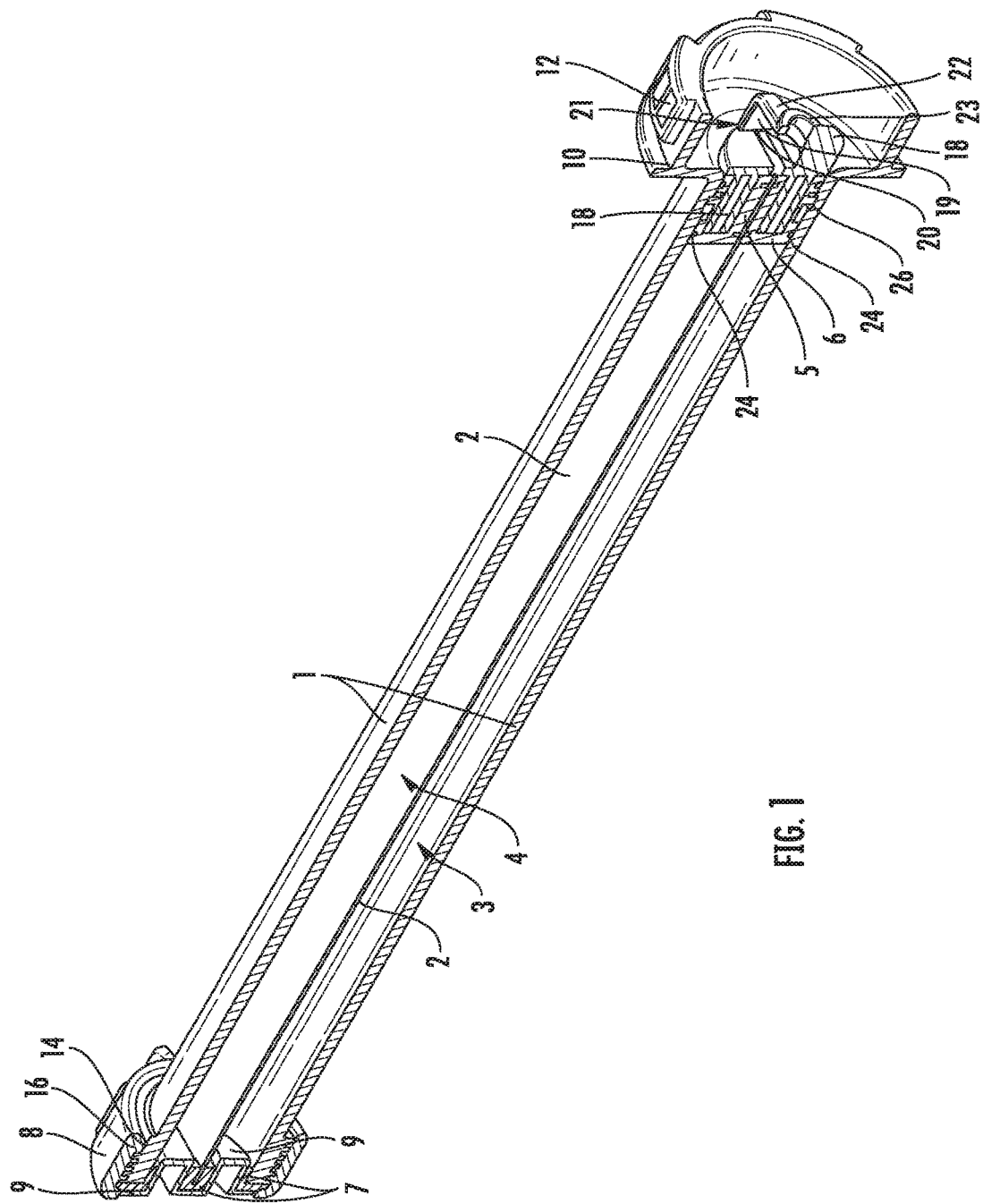
FIG. 1 shows a schematic perspective cross-sectional view of a storage and mixing system according to the invention.

FIG. 1 shows a schematic perspective cross-sectional view of a storage and mixing system according to the invention. The central component of the storage and mixing system is a cylindrical cartridge 1 in which a partition wall 2 connects two opposite inner sides of the inner wall of the cylindrical cartridge 1. The cartridge 1 and the partition wall 2 are designed in one piece as a joint injection-molded part. The partition wall 2 divides the inner space of the cartridge 1 into two separate cavities 3, 4 that are impermeable to fluids, in which the two pasty parent components of a PMMA bone cement are stored.

Figure 5:
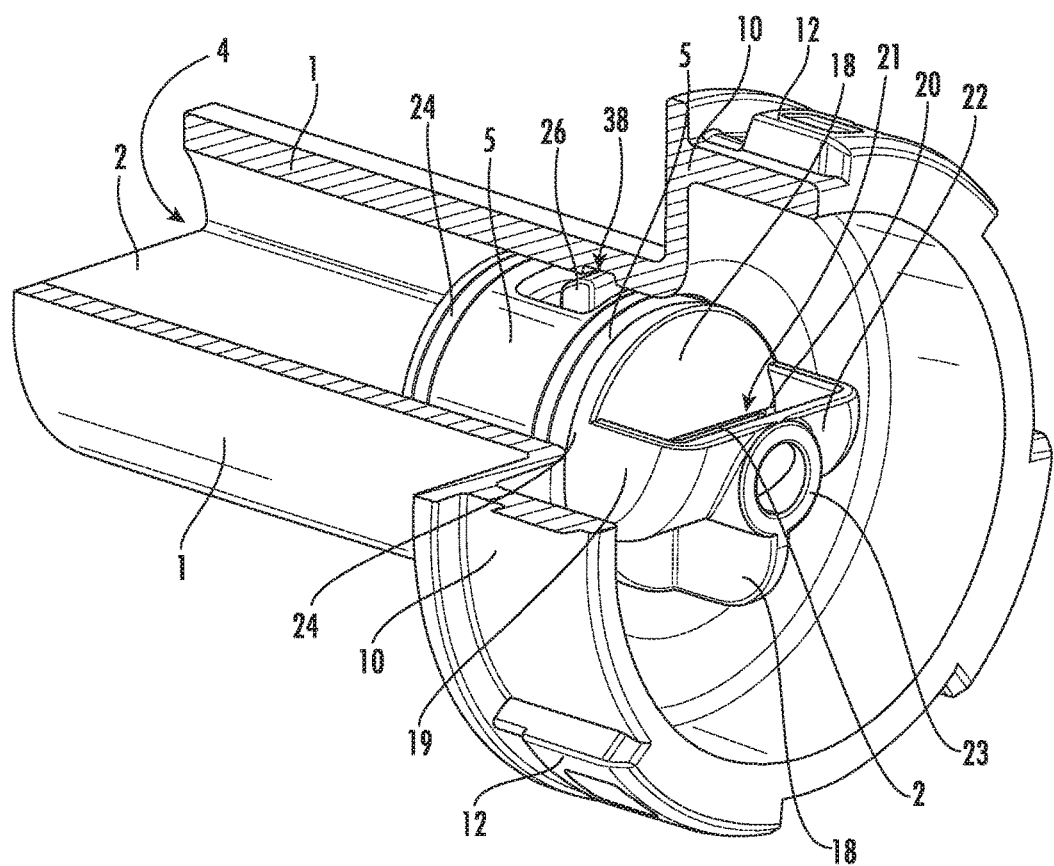
FIG. 5 shows an enlarged schematic perspective cut-open view of the cartridge bottom of the storage and mixing system according to the invention as shown in FIGS. 1, 2 and 4 with the delivery plungers latched and the connecting means inserted.
Figure 9:
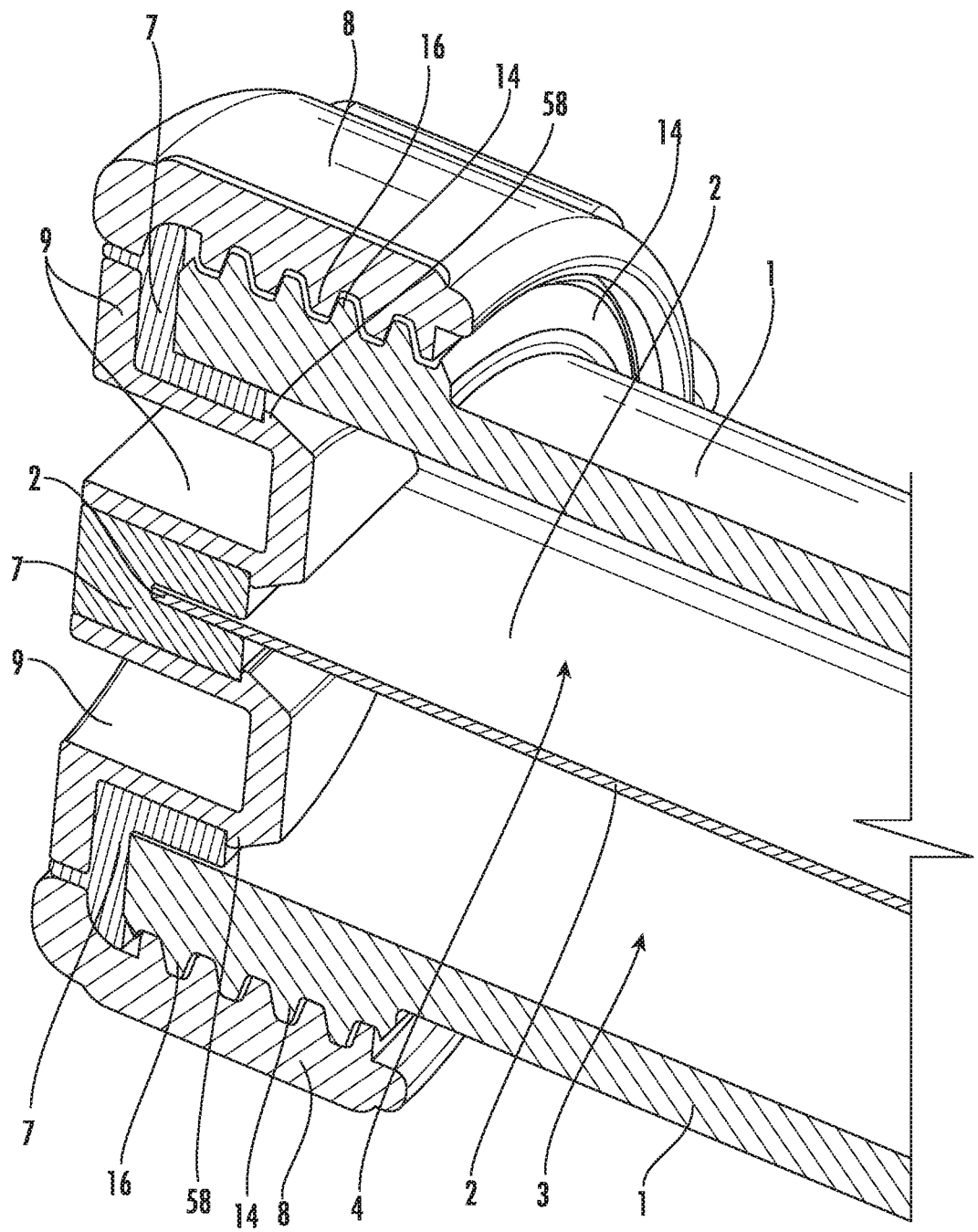
FIG. 9 shows a schematic perspective cross-sectional view of the front part of the storage and mixing system according to the invention as shown in FIGS. 1 and 4 to 8.

The cavities 3, 4 are limited on the rear (see FIG. 1, right) by two delivery plungers 5, 6, wherein the delivery plungers 5, 6 are mounted in an axially movable manner in the two cavities 3, 4. To this end, FIG. 5 shows a detailed view in the form of an enlarged schematic perspective partial cross-sectional view of the cartridge bottom of the storage and mixing system according to the invention as shown in FIG. 1. The two cavities 3, 4 are closed on the front side of the storage and mixing system opposite the delivery plungers 5, 6 by a cartridge head 7 in the form of a rubber-elastic plate 7. The cartridge head 7 is fastened to the front side of the cartridge 1 using a sleeve nut 8 made of plastic. Two ducts are provided in the cartridge head 7, each of which being closed by a plug 9. The cavities 3, 4 are accessible through the two ducts when the plugs 9 are not inserted. FIG. 9 shows a detailed schematic perspective cross-sectional view of the front part of the storage and mixing system according to the invention, wherein the storage and mixing system in FIG. 9 is closed by the cartridge head 7 and the plug 9 therein as in FIG. 1.

On the back side of the cartridge 1, or on its bottom side (on the right in FIG. 1), respectively, a fitting 10 with fastening elements 12 is disposed on the cartridge 1. The cartridge 1 can be connected to a delivery device or applicator (not shown in FIG. 1) via the fitting 10 and the fastening elements 12. On the opposite front side of the cartridge 1 (on the left in FIG. 1), the cartridge head 7 is fastened with a sleeve nut 8 in that a female thread 16 of the sleeve nut 8 is screwed onto a male thread 14 on the cartridge 1. The rubber-elastic plate 7 or cartridge head 7 seals the cavities 3, 4 towards the front.

The cartridge 1 has an outer diameter of 22 mm, an inner diameter of 20 mm, and a length of about 18 cm.

The two delivery plungers 5, 6 are connected on the back sides via a connecting means 18. Two segmented cylindrical ends of the connecting means 18 extend for this purpose towards the cartridge head 7 into matching cavities in the back sides of the delivery plungers 5, 6. The connecting means 18 comprises two outer lateral sleeve walls 19 which laterally delimit the connecting means 18. At the edge the connecting means 18 comprises two cutting edges 20 facing towards the partition wall 2, which cutting edges form an extension of the sleeve walls 19. Between the two cutting edges 20 there is a gap through which the partition wall 2 can slide, if said partition wall is cut off by the cutting edges 20 as a strip from the inner wall of the cartridge 1. An opening 21 which is connected to the gap is configured on the back side of the connecting means 18 between the two sleeve walls 19. The two sleeve walls 19 support a deflecting wall 22 which is inclined to the axis of the storage and mixing system, which deflecting wall forms an inclined deflecting surface 56 internally (see FIGS. 10 and 12). The strip cut off from the partition wall 2 can therefore be pressed through the gap and the opening 21, wherein said strip is pressed by the deflecting surface 56 towards the inner wall of the cartridge 1 and, at the same time, is bent together by the sleeve walls 19. A contact surface 23 for a tappet of a delivery device is formed on the back side of the connecting means 18 (not shown in FIG. 1).

The delivery plungers 5, 6 are sealed by two circumferential seals 24 each made of rubber against the inner wall of the cartridge 1 and against the partition wall 2. A detachable latching element 26 of each of the delivery plungers 5, 6 is connected to a matching mating latching element (in the form of two indentations) in the inner wall of the cartridge 1. The delivery plungers 5, 6 can be pressed by applying pressure from the back side of the cartridge 1 (from the right in FIG. 1) towards the front side of the cartridge 1 (on the left in FIG. 1), that is, in the direction of the cartridge head 7. The latching elements 10 can be detached easily by applying pressure to the bottom side of the delivery plungers 5, 6 when the cartridge head 7 or at least the plugs 9 are removed and are primarily used to prevent the delivery plungers 5, 6 from being pressed out on the bottom side of the cartridge 1 when the inner space of the cartridge 1 is filled with the cement components, or from being pressed towards the cartridge bottom (on the right in FIG. 1) beyond a desired position defined by mating latching elements in the inner wall of the cartridge 1.

Figure 2:
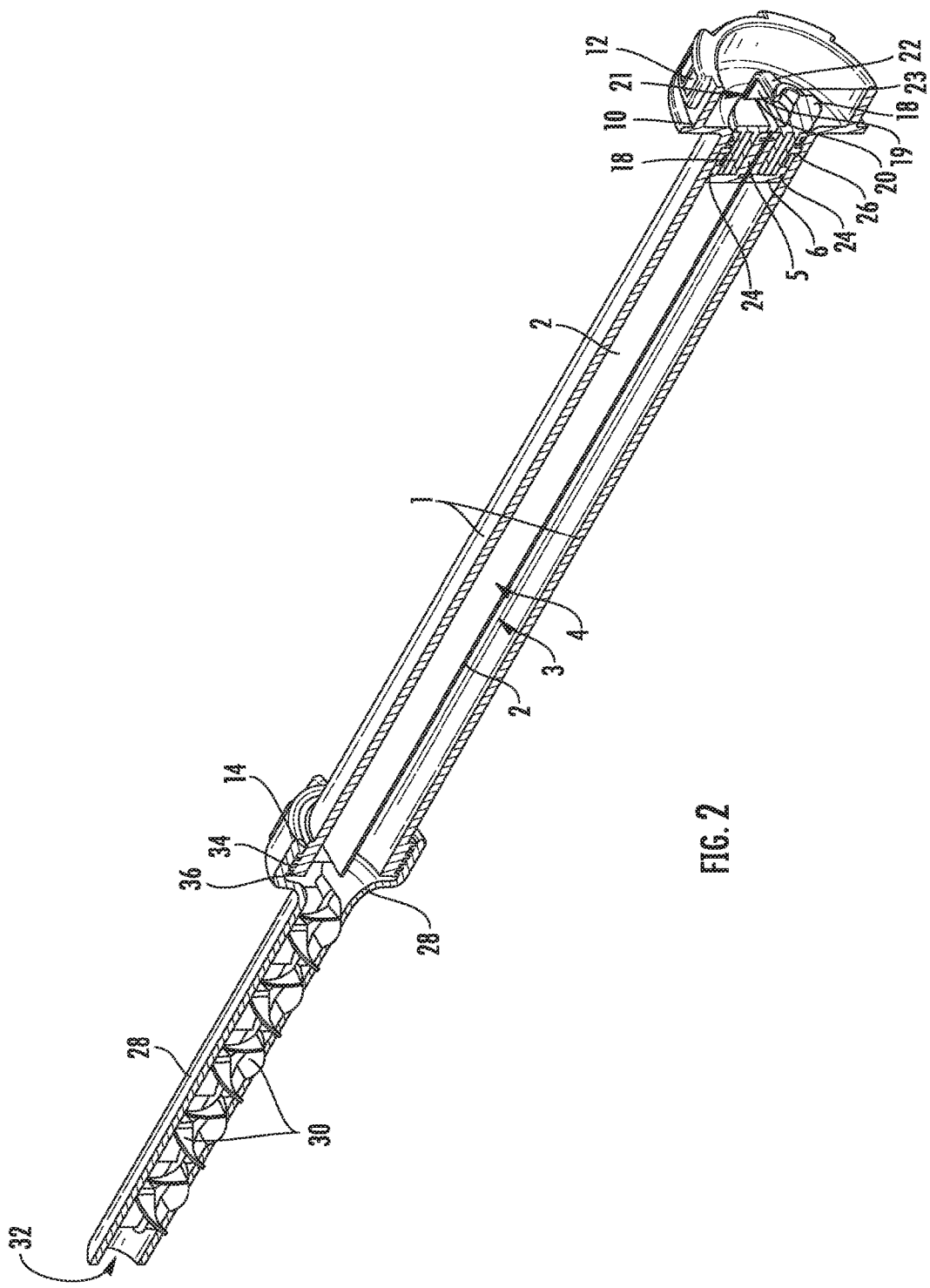
FIG. 2 shows a schematic perspective cross-sectional view of the storage and mixing system according to the invention as shown in FIG. 1 immediately before the application of the PMMA bone cement, in which a delivery pipe is fastened to the cartridge.

FIG. 2 shows a schematic perspective cross-sectional view of the storage and mixing system of FIG. 1 immediately before the application of the PMMA bone cement, in which a delivery pipe 28 is screwed onto the male thread 14 of the cartridge 1. A static mixer 30 with a multitude of twists and mixing elements for mixing the cement components is provided in the delivery pipe 28. The delivery pipe 28 can be even longer than the delivery pipe 28 shown in FIG. 2 to improve accessibility of difficult to access areas, which can be helpful for hip operations, for example. FIG. 2 shows sectional views of all parts except the static mixer 30, a perspective view of which static mixer 30 projects from the section plane.

The cement components are mixed in that they are pressed through the delivery pipe 28 and thus through the static mixer 30. The cement dough produced and mixed in this manner exits via an outlet opening 32 on the tip of the delivery pipe 28. The delivery pipe 28 comprises a female thread 34 that matches the male thread 14 of the cartridge 1, such that the delivery pipe 28 can be stably and firmly connected to the cartridge 1. A sealing ring 36 is disposed between the delivery pipe 28 and the front side of the cartridge 1 such that the cement components cannot exit between the delivery pipe 28 and the cartridge 1. A pressure-stable and pressure-tight connection between the delivery pipe 28 and the cartridge 1 is achieved using threads 14, 34 and the sealing ring 36.

The advance of the delivery plungers 5, 6 is produced by a delivery device (not shown in FIG. 2), which is connected to the fitting 12 and which can be used to manually advance a tappet (see FIGS. 6, 7 and 8) or push rod of the delivery device towards the delivery pipe 28. The tappet then applies pressure to the contact surface 23, such that the delivery plungers 5, 6 are advanced towards the delivery pipe 28 on the one hand, and on the other hand the cutting edges 20 are propelled into the partition wall 2 and cuts the latter off in the process (see FIGS. 7 and 8). The pressure from the tappet disengages the latching elements 10 and propels the delivery plungers 5, 6 forward. The delivery plungers 5, 6 are flush with the inner walls of the cartridge 1 and the partition wall 2. In this way, the content of the cavities 3, 4 of the cartridge 1, that is, the two pasty cement components contained therein, can be pressed out in the forward direction through the delivery pipe 8.

Figure 3:
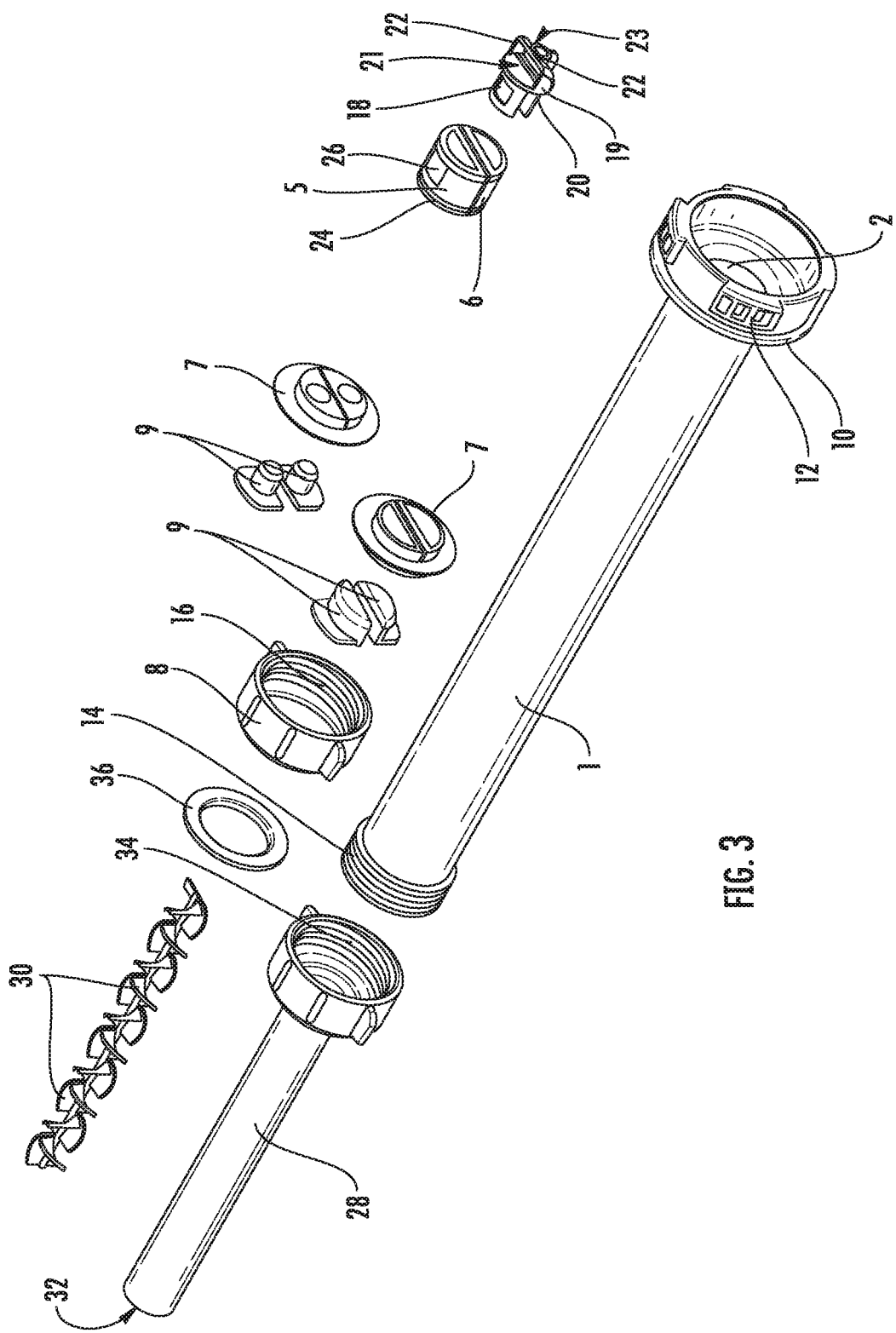
FIG. 3 shows a schematic perspective exploded view of storage and mixing systems according to the invention with twelve different alternative cartridge head variants.

FIG. 3 shows a schematic perspective exploded view of storage and mixing systems according to the invention with twelve alternative and different cartridge heads 7. The design of the storage and mixing systems is similar to the storage and mixing system described above.

FIG. 3 shows two alternative variants of rubber-elastic plates 7 as cartridge heads 7 with ducts formed in different ways that can be closed using different plugs 9. The first variant, which is already shown in FIG. 1, is shown in the bottom left corner relative to the second variant in FIG. 3.

A plug 9 is inserted and latched into each of the ducts. The rubber-elastic plates 7 and the plugs 9 are suitable for building cartridge heads 7 of storage and mixing systems according to the invention. The rubber-elastic plates 7 differ in the shape of their ducts and their plugs 9 which close these ducts. In the first variant (bottom left), the ducts and the plugs 9 have a semicircular or crescent-shaped cross section. In the second variant (on the right above the first variant), the ducts and the plugs 9 have a circular cross section. The free cross section for filling the two cement components is greater in the first variant than in the second. Instead, the geometry in the second variant is adjusted to filling tubes or syringes (not shown) through which the cement components are filled into the cavities 3, 4, such that said filling tubes or syringes are flush with the ducts. The plugs 9 can also be removed to discharge the cement components from the cavities 3, 4 of the cartridge 1 if removing the entire cartridge head 7 is not intended.

In the two variants shown in FIG. 3, flat plastic discs (not shown) can be placed onto the sides of the rubber-elastic plates 7 that face the inner space of the cartridge 1. These plastic discs are used to stabilize the shape of the rubber-elastic plates 7 on the one hand and to improve the chemical stability of the container or the cavities 3, 4 for the cement components on the other.

The tubular cartridge 1 with the partition wall 2, the fitting 10, the fastening elements 12, and the male thread 14 has the same form in all variants. Both the sleeve nut 8 and the delivery pipe 28 can be screwed onto the male thread 14 of the cartridge 1. Variants are conceivable in which the rubber-elastic plate 7 is firmly connected to the cartridge 1 and/or is not rubber-elastic and/or is integral with the cartridge 1. In these cases, no sleeve nut 8 is needed, and the delivery pipe 28 can simply be screwed onto the cartridge 1 after removing the plugs 9. The cement components can then simply be pressed through the ducts into the delivery pipe 28, where they are mixed into the desired cement dough using the static mixer 30.

Figure 4:
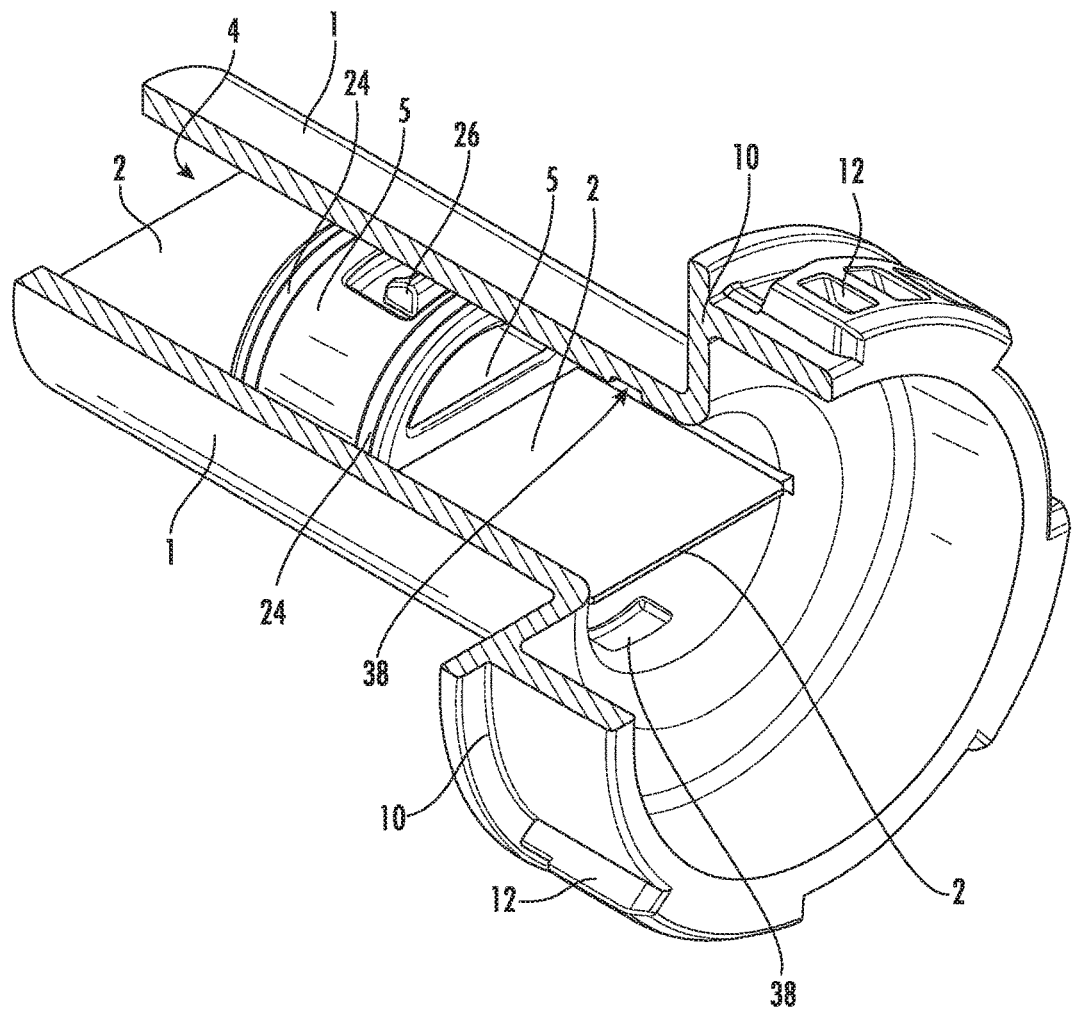
FIG. 4 shows an enlarged schematic perspective cut-open view of the cartridge bottom of the storage and mixing system according to the invention as shown in FIGS. 1 and 2 without the connecting means.

FIGS. 4 to 8 show schematic, partially cut-open perspective views and a cross-sectional view of the cartridge bottom of the storage and mixing system according to the invention as shown in FIGS. 1 and 2 at various stages during advancing of the delivery plungers 5, 6. In FIG. 4, the connecting means 18 is not yet inserted into the bottom of the cartridge 1 and the delivery plungers 5, 6 are not latched into their end positions. The latching means 26 of the delivery plungers 5, 6 namely latch into indentations 38 in the inner wall of the cartridge 1 if they are pushed sufficiently deep in the direction of the rear side of the storage and mixing system into the cavities 3, 4 of the cartridge 1. The latching means 26 block further movement of the delivery plungers 5, 6 towards the back side of the storage and mixing system, while they can still be moved towards the cartridge head 7.

In the position shown in FIG. 5, the latching means 26 of the delivery plungers 5, 6 are latched into place in the indentations 38, and the connecting means 18 is inserted into the bottom sides of the delivery plungers 5, 6 and connects these. This makes the storage and mixing system ready for use. The cartridge head 7 can be detached, or the plugs 9 can be removed from the ducts in the cartridge head 9, and the delivery pipe 28 can be screwed onto the cartridge 1 instead of the sleeve nut 8. In this position, a delivery device can be connected to the fitting 10 or the fastening means 12 of the storage and mixing system. This is shown in FIG. 6.

Figure 6:
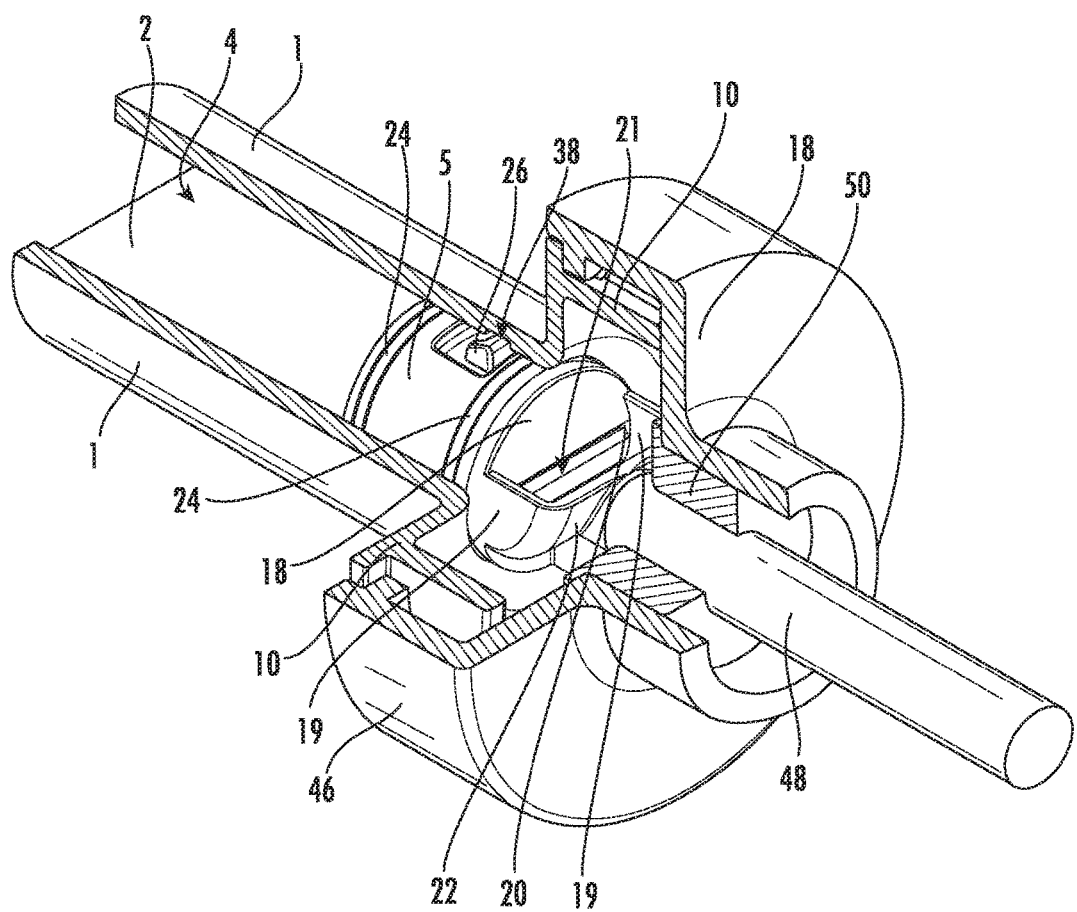
FIG. 6 shows an enlarged schematic perspective cut-open view of the cartridge bottom of the storage and mixing system according to the invention as shown in FIGS. 1, 2, 4 and 5, which is inserted into a delivery device in order to implement a method according to the invention.
Figure 7:
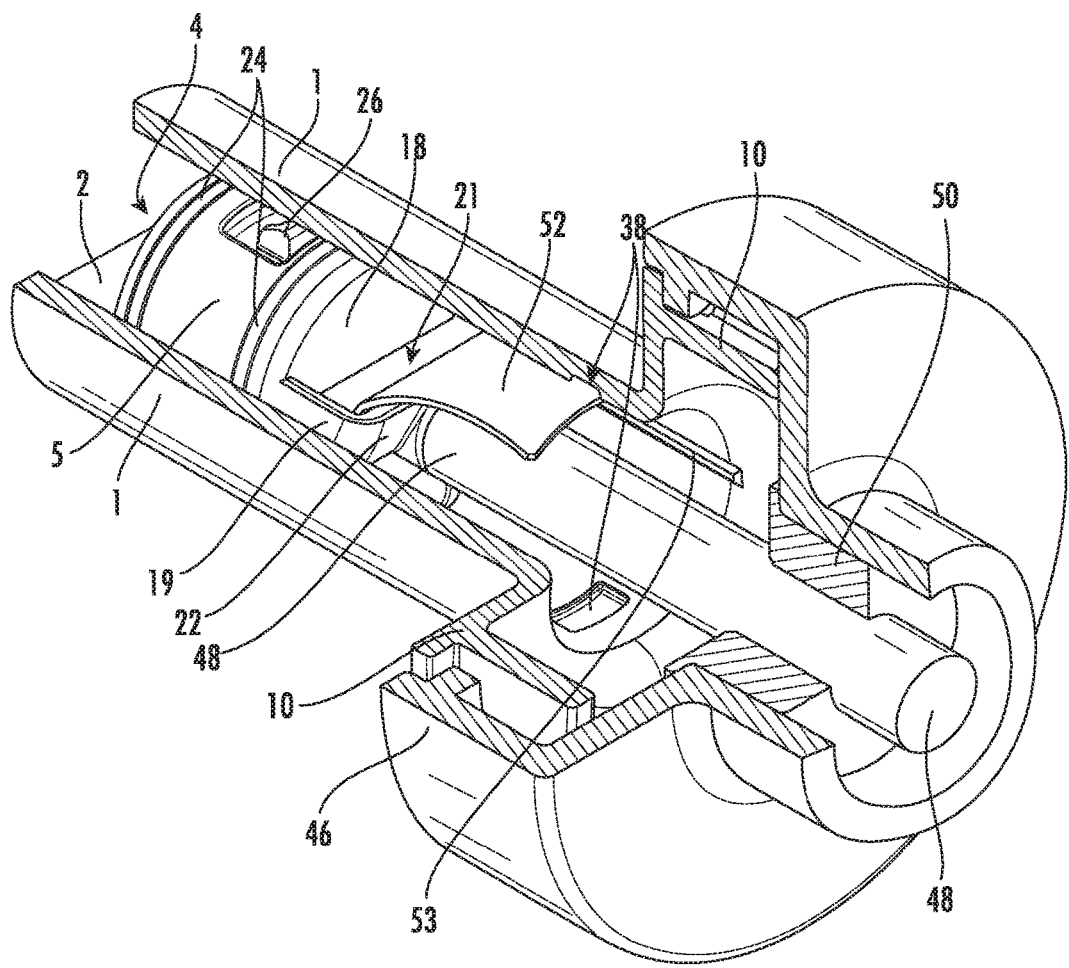
FIG. 7 shows an enlarged schematic perspective cut-open view of the cartridge bottom of the storage and mixing system according to the invention as shown in FIG. 6, in which the tappet of the delivery device has propelled the connecting means and the delivery plungers forwards.
Figure 8:
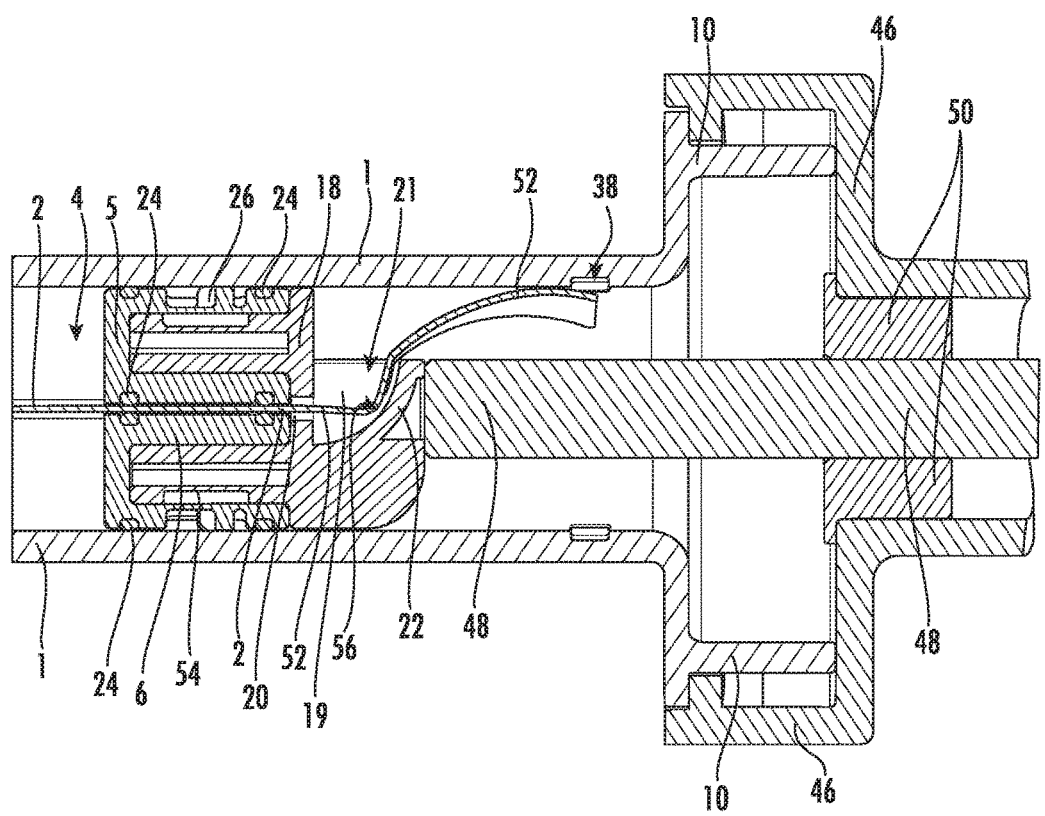
FIG. 8 shows a schematic cross-sectional view of the cartridge bottom of the storage and mixing system according to the invention as shown in FIG. 7.

FIGS. 6, 7 and 8 show two schematic, partially sectional perspective views and a cross-sectional view of the cartridge bottom of the storage and mixing system according to the invention as shown in FIGS. 1, 2, 4 and 5, wherein the storage and mixing system is inserted into a delivery device for implementing a method according to the invention. The only components of the delivery device shown in FIGS. 6, 7 and 8 are a fitting 46 for connecting to the fastening means 12 of the storage and mixing system, a tappet 48, and a bearing 50 for the tappet 48. These parts and the other components of the delivery device correspond to those of typical manually or electrically or pneumatically operated delivery devices. The delivery device has a compartment for receiving the storage and mixing system, wherein said storage and mixing system is held stable at least on the front side in the area of the thread 14 and on the back side at the fitting 10. The fitting 46 is connected with the fastening means 12. The tappet 48, which acts as a push rod 48, can be moved or driven against the fitting 46 of the delivery device, through the fitting 46 or into the cartridge 1, since it is movably held along its longitudinal axis in the bearing 50. The tip of the tappet 48 applies pressure to the contact surface 23 of the connecting means 18. This drives the connecting means 18 and the two delivery plungers 5, 6 forward in the direction of the delivery pipe 28.

The connecting means 18 is advanced by applying pressure to the contact surface 23 in the direction of the cartridge head 7. The latching means 26 detach from the indentations 38 and the delivery plungers 5, 6 are pressed forward in the cavities 3, 4. The two cement components are pressed forward into the delivery pipe 28 and mixed therein. Further advancement of the connecting means 18 not only drives the delivery plungers 5, 6 further in the cavities 3, 4 of the cartridge 1, but the cutting edges 20 begin to cut the partition wall 2 open in the axial direction and, in the process, cut off a strip 56 from the partition wall 2. FIGS. 7 and 8 depict this situation.

The strip 56 is routed through the gap to the deflecting surface 56 or to the deflecting wall 22. A narrow remnant 53 of the partition wall 2 remains on the inner wall of the cartridge 1. When the connecting means 18 is advanced further, the deflecting surface 56 or deflecting wall 22 disposed behind the cutting edges 20 presses the cut-off strip 52 of the partition wall 2 towards the inner wall of the cartridge 1. In the meantime, the cement components are further pressed out of the cavities 3, 4 into the delivery pipe 28 and mixed therein. Finally, the ready-mixed cement dough exits through the outlet opening 32 from the delivery pipe 28 and can be applied to the desired site. Indentations 54 are provided as mating latches 54 in the two limbs of the connecting means 18, which are inserted into the cavities provided for this purpose in the delivery plungers 5, 6, in order to connect these with the connecting means 18 and therefore with one another, said indentations engaging in latching means (not shown) inside the delivery plungers 5, 6. The indentations 54 can be seen particularly well in FIGS. 10 and 11.

Due to the design in accordance with the invention, the resistance against the movement of the tappet 48 does not become great enough to prevent the contents of the cartridge 1 from being pressed out using conventional and also manually operated delivery devices, despite the high viscosity of the pasty cement components, the flow resistance caused by the static mixer 30, and despite the force or energy required for cutting the partition wall 2 with the cutting edges 20.

As can be seen in FIG. 9, the plugs 9 include a latching means 42 in the form of projections that engage over the edge of the ducts into the inner space of the cartridge 1 in the cartridge head 7 and thus interlock with the cartridge head 7. The latching means 58 ensures that the plugs 9 will not inadvertently detach from the cartridge head 7.

Figure 10:
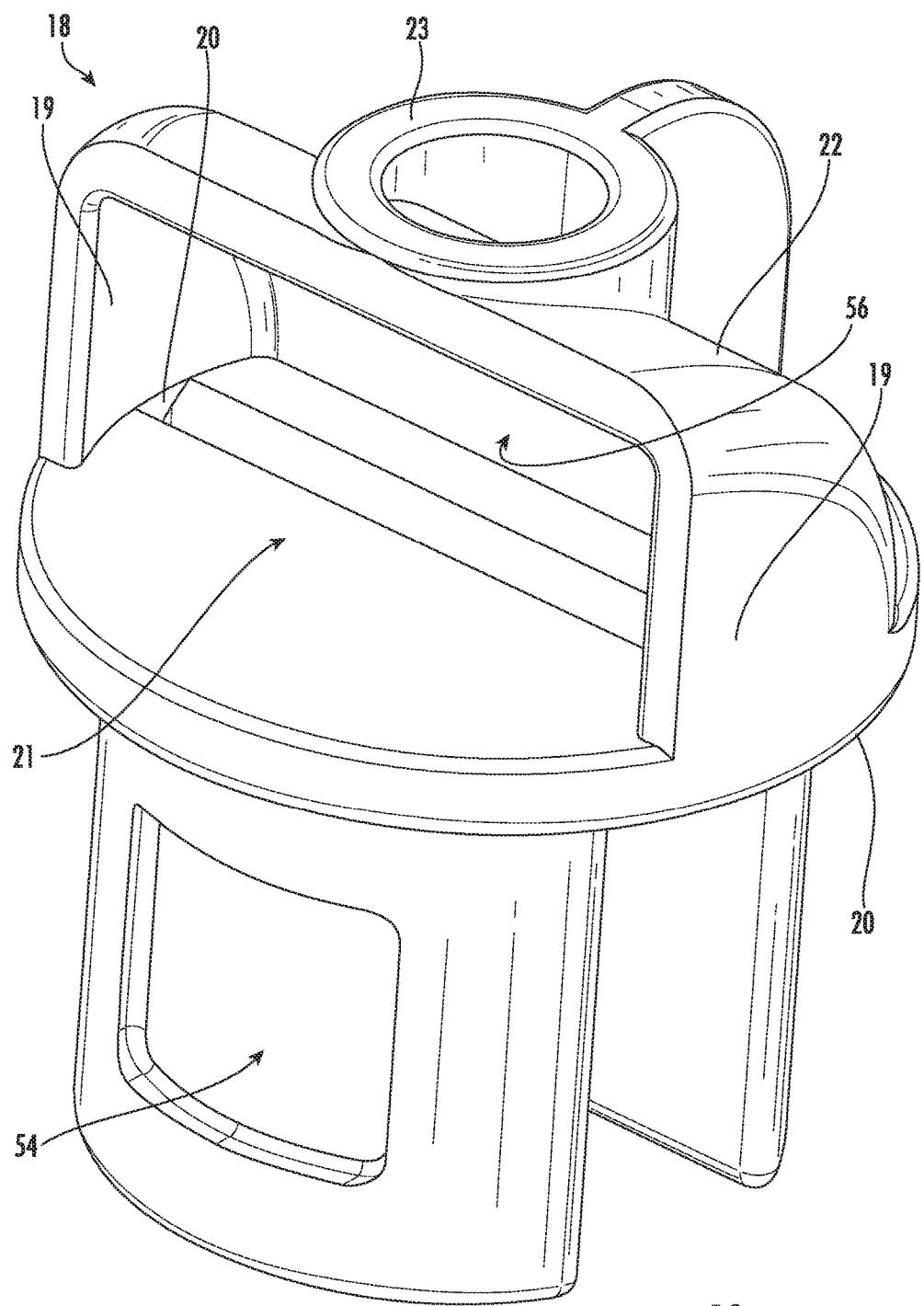
FIGS. 10 and 11 show two schematic perspective views of a connecting means for a storage and mixing system according to the invention.
Figure 11:
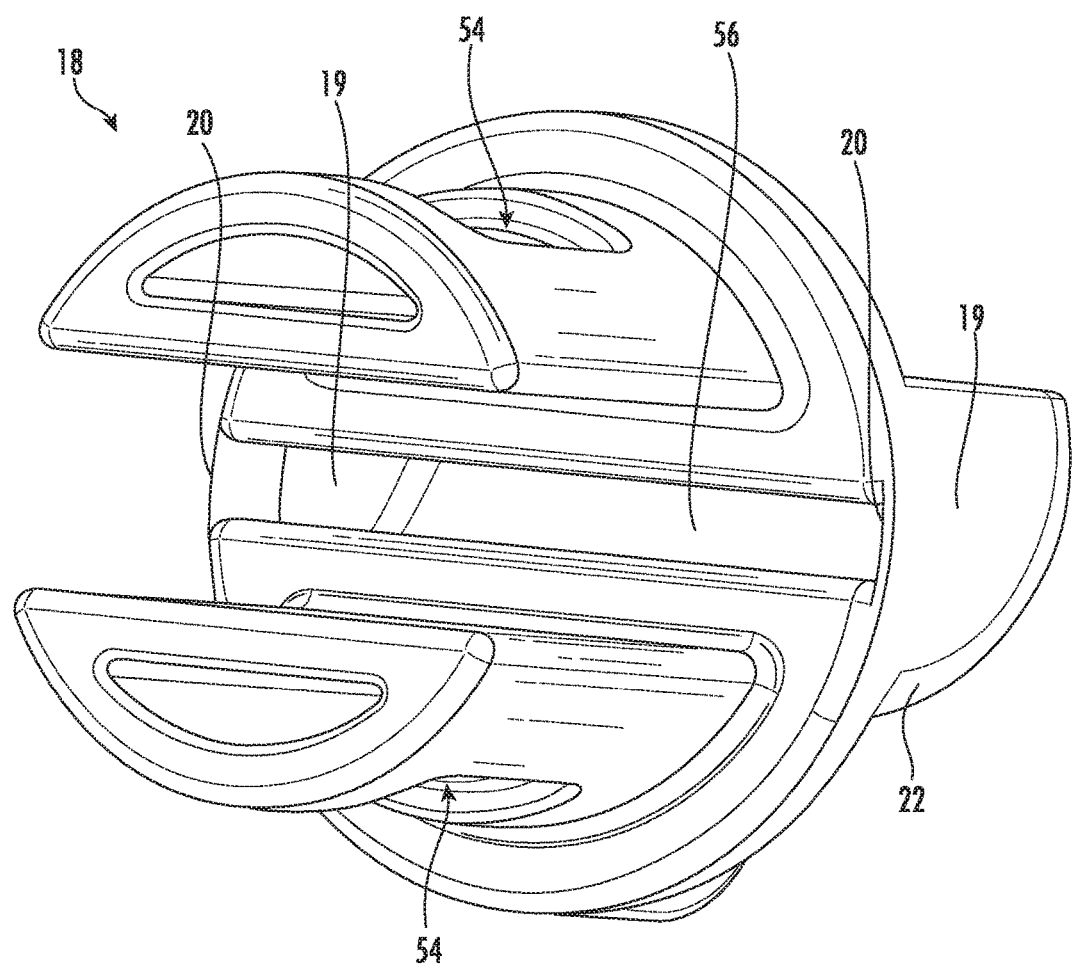
Figure 12:
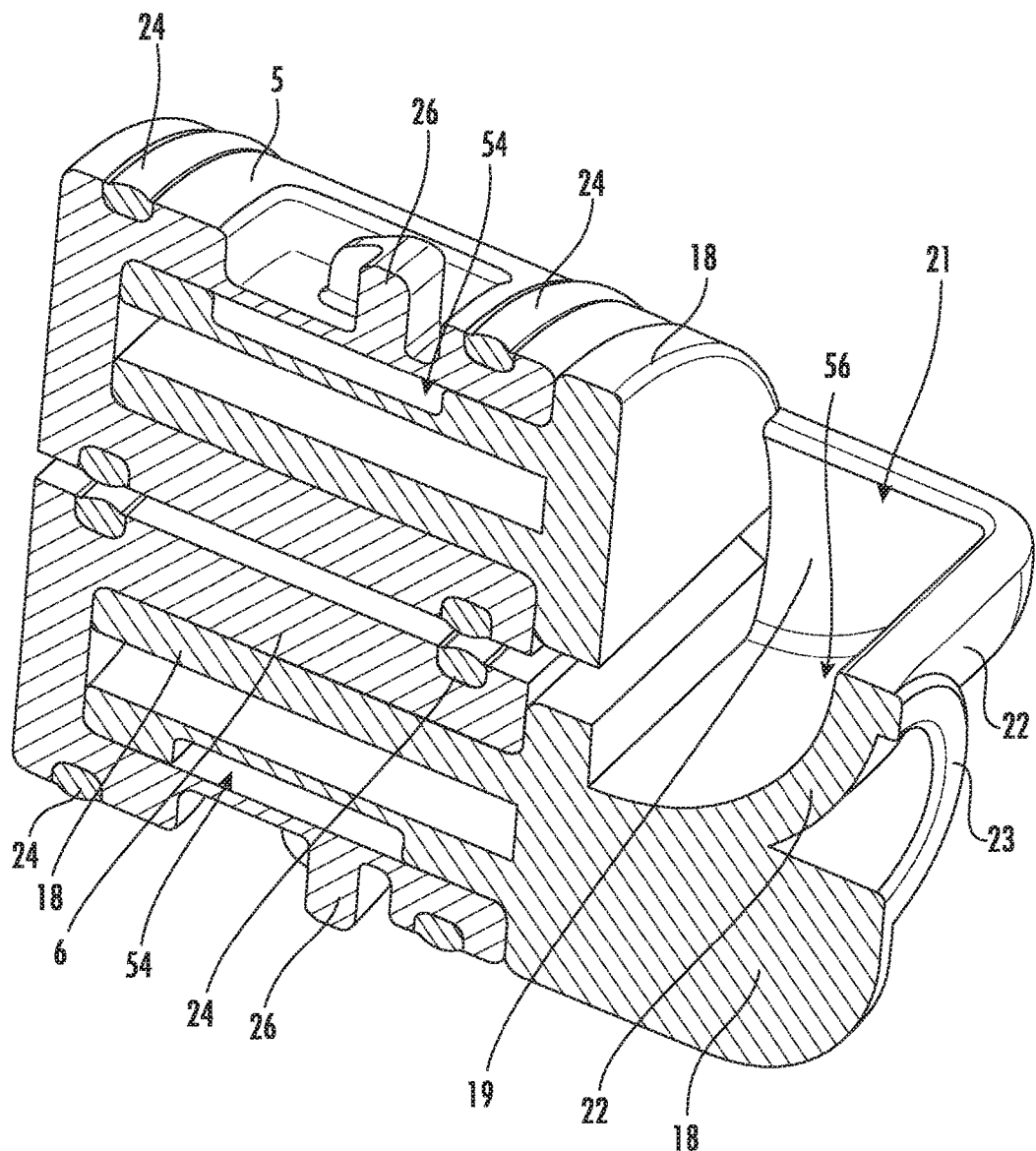
FIG. 12 shows a schematic perspective view of the connecting means as shown in FIGS. 10 and 11, which is connected to two delivery plungers.

FIGS. 10 and 11 show two perspective views of a connecting means 18 for a storage and mixing system according to the invention, and FIG. 12 shows a schematic perspective view of the connecting means 18 of FIGS. 10 and 11, which are connected to two delivery plungers 5, 6. The connecting means 18 has roughly the shape of a yoke and comprises a mirror plane as a symmetry plane, wherein the axis of the storage and mixing system is in the mirror plane.

The side of the connecting means 18 that is facing the cartridge head 7 consists of two cylinder segments that are cut in one plane parallel to the cylinder axis, wherein the two indentations 44 are disposed on the circumferential surface of the cylinder segments as mating latches 54 for one latching means each in the delivery plungers 5, 6. The two cylinder segments of the connecting means 18 therefore latch with the delivery plungers 5, 6 when the openings provided for this purpose are inserted in the back side of the delivery plungers 5, 6 opposite the cartridge head 7.

The two cylinder segments are connected to one another by means of a circular plate. In the plate, there is located the gap which is provided for conducting through the cut-off strip 40 of the partition wall 2, i.e. it aligns with the partition wall 2 in the installed condition. The two sleeve walls 19, which connect the inclined deflecting wall 22 with the deflecting surface 56 on the inside of the deflecting wall 22, extend on the plate. The plate, the sleeve walls 19 and the deflecting wall 22 delimit the opening 21, through which the re-routed and bent strip 40 of the partition wall 2 moves, while the connecting means 18 is moved forwards towards the delivery pipe 28. The two cutting edges 20, which cut off the partition wall 2 in the area of the inner wall of the cartridge 1, are located on both sides of the gap.

A central vertical cylinder with a circular basis 23, which forms the contact surface 23 for a tappet 48 (see FIGS. 6, 7 and 8) of a delivery device, is located in the center on the back side of the plate. The two cylinder segments are kept at a fixed distance from each other by the plate and the sleeve walls 19. The distance is selected such that the two delivery plungers 5, 6 are kept apart at a distance that is slightly smaller than, and at most equal to, the thickness of the partition wall 2, for example 1 mm, when they are positioned on the cylinder segments of the connecting means 18. The cutting edges 20 can be inserts made of a hard metal or hard plastic, or the entire connecting means 18 can be made of such a material that has to be hard enough to cut off the partition wall 2 when the connecting means 18 is advanced in the cartridge 1 towards the cartridge head 7.

The cartridge 1 and the fitting 10 are preferably designed in one piece and made of plastic for all variants. All parts of the storage and mixing system can be injection-molded from plastic, except for the seals 24. The seals 24 are preferably made of rubber. The plate 7 for the cartridge head 7 can also be made of rubber or a rubber-elastic material. The cutting edges 20 preferably consist of a metal, a ceramic material, a metal alloy, or a particularly hard plastic material. All other parts of the storage and mixing system can theoretically be made of metallic materials. Preferred cement components for use are pasty parent components of a PMMA bone cement. Other cements, such as dental cements, two-component adhesives or other two-component systems that are mixed of pasty parent components can theoretically be stored and mixed using a storage and mixing system according to the invention.

The features of the invention disclosed in the above description, the claims, figures, and exemplary embodiments can be relevant both individually and in combination for implementing the various embodiments of the invention.

LIST OF REFERENCE SYMBOLS

1 Cartridge
2 Partition wall
3 Cavity

4 Cavity
5 Delivery plunger
6 Delivery plunger
7 Cartridge head
8 Sleeve nut
9 Plug
10 Fitting
12 Fastening element
14 Male thread
16 Female thread
18 Connecting means
19 Sleeve wall
20 Cutting edge
21 Opening
22 Inclined deflecting wall
23 Contact surface
24 Seal
26 Latching means
28 Delivery pipe
30 Static mixer
32 Outlet opening
34 Female thread
36 Seal
38 Mating latching means/indentation
46 Fitting
48 Tappet/push rod
50 Bearing
52 Cut-open partition wall
53 Partition wall remnant/partition wall projection
54 Indentation/mating latch
56 Inclined deflecting surface
58 Latching means

We claim:

1. A storage and mixing system for pasty two-component polymethyl methacrylate bone cements, the storage and mixing system comprising:
a tubular cartridge with a cylindrical interior;
a cartridge head that closes one end of the tubular cartridge;
a partition wall axially disposed in the cylindrical interior of the cartridge, wherein the partition wall is connected to the circumferential surface of the cylindrical interior of the cartridge and divides the cylindrical interior of the cartridge delimited by the cartridge head into two spatially separate cavities, wherein the first cavity includes a first pasty cement component and the separate second cavity includes a second pasty cement component; and
two delivery plungers disposed movably in the axial direction in the two cavities of the cartridge, wherein the delivery plungers close the two cavities on the side of the cavities opposite the cartridge head,
wherein
the delivery plungers on the back side opposite the cartridge head are connected to one another via a sleeve-shaped connecting means, wherein at least two cutting edges are disposed on the front side of the sleeve-shaped connecting means facing the cartridge head such that the at least two cutting edges cut off the partition wall from the cylindrical inner wall of the cartridge as at least one cut-off strip if the delivery plungers are advanced towards the cartridge head in the cavities with the connecting means,
the sleeve-shaped connecting means comprises a sleeve wall and a deflecting surface which is inclined to the axis of the connecting means which, if the connecting means is advanced, presses the at least one cut-off strip of the partition wall towards the inner wall of the cartridge,
the inclined deflecting surface is in certain areas enclosed by the sleeve wall of the sleeve-shaped connecting means such that the at least one cut-off strip of the partition wall running through the connecting means is curved by the sleeve wall of the connecting means which encloses the inclined deflecting surface about the longitudinal axis of the at least one cut-off strip.

2. The storage and mixing system according to claim 1, wherein the partition wall is connected to the circumferential surface of the cylindrical interior of the cartridge along two connecting lines which delimit the circumferential surface, wherein these connecting lines are arranged opposite one another and the axis of the cartridge extends in the partition wall.

3. The storage and mixing system according to claim 1, wherein the cavities have a semicircular or circular segmental cross section and the delivery plungers have a matching cross section such that the delivery plungers close the cavities at each axial position in the cavities.

4. The storage and mixing system according to claim 1, wherein the delivery plungers are spaced apart by the connecting means such that the gap between the delivery plungers is smaller than or equal to the thickness of the partition wall.

5. The storage and mixing system according to claim 1, wherein the partition wall has a maximum thickness of 1.5 mm and/or a thickness such that the partition wall is cuttable by the at least two cutting edges on which a driving force of 1 kN acts.

6. The storage and mixing system according to claim 1, further comprising:
a delivery pipe that is provided with a fastening means for fastening the delivery pipe to the cartridge, wherein the delivery pipe is fixable to the cartridge instead of the cartridge head.

7. The storage and mixing system according to claim 6, wherein a ratio of the diameter of the interior of the cartridge to the inner diameter of the delivery pipe is smaller than 5 to 2.

8. The storage and mixing system according to claim 1, wherein a diameter of the interior of the cartridge is smaller than or equal to 25 mm.

9. The storage and mixing system according to claim 1, wherein the cartridge is integral with the partition wall disposed inside it and/or the cartridge and the partition wall are made from plastic as a one-piece injection-molded part.

10. The storage and mixing system according to claim 1, wherein the at least two cutting edges consist of at least one selected from a steel alloy, aluminum alloy, tin alloy, ceramic, a polyamide, glass fiber reinforced polyamide, polyimide, polyamide co-imide, polyether ketone and polysulfone.

11. The storage and mixing system according to claim 1, further comprising:
two ducts provided in the cartridge head connect the two cavities to the environment of the storage and mixing system, wherein a detachable plug is disposed in each of these ducts.

12. The storage and mixing system according to claim 1, wherein the cartridge comprises a fastening element for a delivery device on the side opposite the cartridge head and at least one fastening means on the side of the cartridge head selected from a male thread, a female thread, at least one element of a bayonet joint and/or a latching element of a latching closure as a fastening means.

13. The storage and mixing system according to claim 1, wherein the cartridge, the cartridge head, the partition wall and the delivery plungers are made of a plastic material selected from polyethylene co-vinyl alcohol (EVOH), polybutylene terephthalate (PBT), polyethylene terephthalate (PET) and polymethacrylic acid methyl ester-co-acrylonitrile.

14. The storage and mixing system according to claim 1, wherein the cartridge head is realized by an rubber-elastic plate that is fastened to the cartridge using a sleeve cap, wherein said sleeve cap blocks movement of the rubber-elastic plate away from the cartridge by means of a projecting rim, and wherein said rubber-elastic plate has a recess for receiving the longitudinal side of the partition wall on the side facing the delivery plungers, and wherein said recess in the rubber-elastic plate defines two areas, wherein a duct that is closed by a plug is disposed in each area.

15. The storage and mixing system according to claim 1, further comprising:
a sleeve cap provided as a connecting element for connecting the cartridge head to the cartridge, wherein the sleeve cap includes a female thread or a male thread or a bayonet joint or latching elements.

16. The storage and mixing system according to claim 1, wherein the sleeve-shaped connecting means on the back side that faces away from the cartridge head comprises a lateral opening such that the at least one strip of the partition wall cut off from the inner wall of the cartridge exits through said opening laterally out of the connecting means.

17. The storage and mixing system according to claim 1, wherein the sleeve-shaped connecting means on the side facing the cartridge head circumferentially rests against the inner wall of the interior of the cartridge.

18. A method, for mixing pasty cement components of a polymethyl methacrylate bone cement, utilizing the storage and mixing system according to claim 1, the method successively comprising:
a) removing the cartridge head from the cartridge or removing at least two plugs from at least two ducts in the cartridge head such that the cartridge is opened,
b) arranging and connecting a delivery pipe to the opened cartridge, wherein the delivery pipe includes a mixer,
c) inserting the cartridge into a manually operated delivery device, the delivery device comprising a tappet that is drivable in the axial direction to advance the delivery plungers in the cavities of the cartridge, and
d) extruding the pasty cement components by means of the delivery device through the axial advancement of the delivery plungers using the tappet, as a result of which the cement components are pressed into the delivery pipe, wherein the two cement components are mixed into a pasty cement dough by the mixer in the delivery pipe and the mixed cement dough flows out of an outlet opening of the delivery pipe, wherein
the partition wall is cut off by the at least two cutting edges in the longitudinal direction of the cartridge in sync with the movement of the delivery plungers,
the at least one cut-off strip of the partition wall is pressed at least sufficiently towards the inner wall of the cartridge with the deflecting surface that further movement of the tappet of the delivery device is not prevented or hindered by the at least one strip, and
the at least one strip of the partition wall is curved by the sleeve wall of the connecting means which encloses the inclined deflecting surface about the longitudinal axis of the at least one cut-off strip.

19. The method according to claim 18, wherein a connecting element that connects the cartridge head to the cartridge is loosened to remove the cartridge head from the cartridge in a).

20. The method according to claim 18, wherein the delivery pipe is connected to the cartridge by connecting a connecting element of the delivery pipe to a connecting element of the cartridge.

21. The method according to claim 18, wherein the tappet of the delivery device applies pressure to the side of the connecting means that faces away from the delivery plungers and that the delivery plungers are driven via the connecting means.

22. The method according to claim 18, wherein the side of the connecting means that faces away from the delivery plungers comprises a contact surface for making contact with the front side of the tappet or of a tray attached to the same, said contact surface being of equal size or greater than the cross section of the tappet or the support surface of the tray, wherein said contact surface covers the cross section of the tappet or the support surface of the tray if the tappet is advanced or the contact surface exceeds the cross section of the tappet or the supporting surface of the tray.

23. The method according to claim 18, wherein the at least two cutting edges cut off the partition wall at a distance of not more than 1 mm from the inner wall of the cartridge off the inner wall of the cartridge.

24. The method according to claim 18, wherein the applicator is manually drivable or is drivable by compressed air or electrically drivable.

\* \* \* \* \*